(12) United States Patent
Kim et al.

(10) Patent No.: US 10,647,753 B2
(45) Date of Patent: May 12, 2020

(54) INSULIN ANALOGS AND USE THEREOF

(71) Applicant: HANMI PHARM. CO., LTD, Hwaseong-si, Gyeonggi-do (KR)

(72) Inventors: Jin Young Kim, Hwaseong-si (KR); Euh Lim Oh, Hwaseong-si (KR); Jong Soo Lee, Hwaseong-si (KR); Hyung Kyu Lim, Hwaseong-si (KR); In Young Choi, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 15/990,495

(22) Filed: May 25, 2018

(65) Prior Publication Data

US 2018/0282388 A1 Oct. 4, 2018

Related U.S. Application Data

(63) Continuation of application No. 15/250,459, filed on Aug. 29, 2016, now Pat. No. 10,017,557.

(30) Foreign Application Priority Data

Aug. 28, 2015 (KR) .................. 10-2015-0121819

(51) Int. Cl.
| | | |
|---|---|---|
| *A61K 38/28* | (2006.01) | |
| *A61K 38/16* | (2006.01) | |
| *A61K 38/00* | (2006.01) | |
| *C07K 14/62* | (2006.01) | |
| *C07K 14/00* | (2006.01) | |

(52) U.S. Cl.
CPC .............. *C07K 14/62* (2013.01); *A61K 38/00* (2013.01)

(58) Field of Classification Search
CPC ........ A61K 38/00; A61K 38/28; A61K 38/16; C07K 14/62; C07K 14/00
USPC .............. 514/5.9, 6.2, 6.3, 6.7, 6.8, 6.9, 7.3; 530/303, 324

See application file for complete search history.

(56) References Cited

U.S. PATENT DOCUMENTS

| | | |
|---|---|---|
| 5,175,145 A | 12/1992 | Cooper |
| 5,422,339 A | 6/1995 | Eisenbarth et al. |
| 5,424,286 A | 6/1995 | Eng |
| 5,716,927 A | 2/1998 | Balschmidt et al. |
| 6,403,764 B1 | 6/2002 | Dubaquie et al. |
| 7,736,653 B2 | 6/2010 | Kim et al. |
| 7,790,677 B2 | 9/2010 | Zimmerman et al. |
| 8,476,230 B2 | 6/2013 | Song et al. |
| 8,703,701 B2 | 4/2014 | DiMarchi |
| 9,165,768 B2 | 10/2015 | Kang |
| 9,341,445 B2 | 5/2016 | de Haas et al. |
| 9,422,349 B2 | 8/2016 | Jung et al. |
| 9,526,764 B2 | 12/2016 | Werner et al. |
| 9,528,180 B2 | 12/2016 | Becker et al. |
| 9,669,073 B2 | 6/2017 | Kim et al. |
| 2005/0288248 A1 | 12/2005 | Pan et al. |
| 2006/0241019 A1 | 10/2006 | Bridon et al. |
| 2010/0105877 A1 | 4/2010 | Song et al. |
| 2010/0216692 A1 | 8/2010 | Brunner-Schwarz et al. |
| 2011/0077197 A1 | 3/2011 | Habermann et al. |
| 2011/0152185 A1 | 6/2011 | Plum et al. |
| 2011/0257091 A1 | 10/2011 | DiMarchi et al. |
| 2012/0021978 A1 | 1/2012 | Werner et al. |
| 2012/0071402 A1 | 3/2012 | Madsen et al. |
| 2012/0100141 A1 | 4/2012 | Herring et al. |
| 2012/0184488 A1 | 7/2012 | Weiss |
| 2013/0028918 A1 | 1/2013 | Song et al. |
| 2013/0122023 A1 | 5/2013 | Woo et al. |
| 2014/0120120 A1 | 5/2014 | Woo et al. |
| 2014/0212440 A1 | 7/2014 | Jung et al. |
| 2015/0190528 A1 | 7/2015 | Lim et al. |
| 2016/0008483 A1 | 1/2016 | Hwang et al. |
| 2017/0143802 A1 | 5/2017 | Kim et al. |

FOREIGN PATENT DOCUMENTS

| | | |
|---|---|---|
| CL | 1235-2003 | 4/2004 |
| CL | 0018-2009 | 6/2009 |
| CL | 201603075 | 11/2016 |
| CN | 1571676 A | 1/2005 |
| CN | 1635900 A | 7/2005 |
| CN | 101861333 A | 10/2010 |
| CN | 102256618 A | 11/2011 |
| CN | 102711805 A | 10/2012 |
| CN | 103596595 A | 2/2014 |
| CN | 103732616 A | 4/2014 |

(Continued)

OTHER PUBLICATIONS

Japanese Patent Office; Communication dated Mar. 5, 2019 in application No. 2016-569949.
Intellectual Property Office of Taiwan; Communication dated May 1, 2019 in application No. 104117389.
Intellectual Property Office of Singapore; Communication dated Apr. 9, 2019 in application No. 11201609872Y.

(Continued)

*Primary Examiner* — Julie Ha
(74) *Attorney, Agent, or Firm* — Sughrue Mion, PLLC

(57) ABSTRACT

An insulin analog with an improved in vitro effect compared with native insulin, a pharmaceutical composition for treating diabetes containing the insulin analog as an active ingredient, and a method for treating diabetes using the insulin analog or the pharmaceutical composition are described. A nucleic acid encoding the insulin analog, an expression vector including the nucleic acid, a transformant introduced with the expression vector, and a method of producing the insulin analog from the transformant are also described.

6 Claims, 3 Drawing Sheets
Specification includes a Sequence Listing.

(56) References Cited

FOREIGN PATENT DOCUMENTS

| | | | |
|---|---|---|---|
| CN | 103736082 A | 4/2014 | |
| DE | 25 36 040 A1 | 2/1977 | |
| DE | 10227232 A1 | 1/2004 | |
| DE | 102008003568 A1 | 7/2009 | |
| DE | 102008025008 A1 | 11/2009 | |
| EP | 2017288 A1 | 1/2009 | |
| EP | 2700654 A1 | 2/2014 | |
| EP | 2963056 A1 | 1/2016 | |
| JP | 2009-504169 A | 2/2009 | |
| JP | 2010-533671 A | 10/2010 | |
| JP | 2011-515358 A | 5/2011 | |
| JP | 2012-62311 A | 3/2012 | |
| JP | 2012-229214 A | 11/2012 | |
| KR | 10-2005-0121748 A | 12/2005 | |
| KR | 10-0725315 B1 | 6/2007 | |
| KR | 10-2010-0111683 A | 10/2010 | |
| KR | 10-2011-0084956 A | 7/2011 | |
| KR | 10-2011-0092253 A | 8/2011 | |
| KR | 10-1058209 B1 | 8/2011 | |
| KR | 10-1058290 B1 | 8/2011 | |
| KR | 10-2011-0111267 A | 10/2011 | |
| KR | 10-2011-0134210 A | 12/2011 | |
| KR | 10-2011-0137819 A | 12/2011 | |
| KR | 1020110134209 A | 12/2011 | |
| KR | 10-2012-0135123 A | 12/2012 | |
| KR | 10-2012-0137271 A | 12/2012 | |
| KR | 10-2012-0139579 A | 12/2012 | |
| KR | 10-1231431 B1 | 2/2013 | |
| KR | 10-1324828 B1 | 11/2013 | |
| KR | 10-1330868 B1 | 11/2013 | |
| KR | 10-2014-0006938 A | 1/2014 | |
| KR | 10-2014-0022909 A | 2/2014 | |
| KR | 10-2014-0106452 A | 9/2014 | |
| TW | 201204382 A1 | 2/2012 | |
| WO | 96/32478 A1 | 10/1996 | |
| WO | 97/34631 A1 | 9/1997 | |
| WO | WO-2008034881 A1 * | 3/2008 | ............ C07K 14/62 |
| WO | 2009/022005 A1 | 2/2009 | |
| WO | 2009/129250 A2 | 10/2009 | |
| WO | 2010/080606 A1 | 7/2010 | |
| WO | 2010/080609 A1 | 7/2010 | |
| WO | 2011/028813 A2 | 3/2011 | |
| WO | 2011122921 A2 | 10/2011 | |
| WO | 2012/015692 A2 | 2/2012 | |
| WO | 2012/098462 A1 | 7/2012 | |
| WO | 2012/165915 A2 | 12/2012 | |
| WO | 2012/167251 A1 | 12/2012 | |
| WO | 2012/169798 A2 | 12/2012 | |
| WO | 2012/173422 A1 | 12/2012 | |
| WO | 2013/110069 A1 | 7/2013 | |
| WO | 2013/133667 A1 | 9/2013 | |
| WO | 2014/017843 A1 | 1/2014 | |
| WO | 2014/017845 A2 | 1/2014 | |
| WO | 2014/017847 A1 | 1/2014 | |
| WO | 2014/017849 A1 | 1/2014 | |
| WO | 2014/049610 A2 | 4/2014 | |
| WO | 2014/073842 A1 | 5/2014 | |
| WO | 2014/133324 A1 | 9/2014 | |
| WO | 2015108398 A1 | 7/2015 | |
| WO | 2015/183038 A1 | 12/2015 | |

OTHER PUBLICATIONS

Wolfgang Glaesner et al., "Engineering and characterization of the long-acting glucagon-like peptide-1 analogue LY2189265, an Fc fusion protein", Diabetes/Metabolism Research and Reviews, vol. 26, 2010, pp. 287-296.

"CADTH Optimal Use Report: Combination Use of Insulin and Incretins in Type 2 Diabetes", Canadian Agency for Drugs and Technologies in Health, vol. 3, Issue 1C, Jul. 2013, pp. i-ii, 1-18 (22 pages total).

Fabio Selis et al., "Enzymatic mono-pegylation of glucagon-like peptide 1 towards long lasting treatment of type 2 diabetes", Results in Pharma Sciences 2, Elsevier, 2012, pp. 58-65.

C. Schmid et al., "Increased insulin dose requirement of long-acting insulin analogues in obese patients with type 2 diabetes", Diabetologia, vol. 52, 2009, pp. 2668-2669.

Bhat et al., "A novel GIP-oxyntomodulin hybrid peptide acting through GIP, glucagon and GLP-1 receptors exhibits weight reducing and anti-diabetic properties", Biochem Pharmacol, Jun. 1, 2013, vol. 85 No. 11, pp. 1655-1662.

Intellectual Property Office of Singapore; Communication dated Jul. 15, 2019 in app No. 11201802523X.

Ministry of Law and Human Rights Republic of Indonesia; Communication dated Jun. 12, 2019 in application No. P00201608768.

Intellectual Property Office of Taiwan; Communication dated May 13, 2019 in application No. 104117391.

European Patent Office; Communication dated Jul. 19, 2019 in application No. 16842233.5.

Japanese Patent Office; Communication dated Jul. 4, 2019 in application No. 2016-570276.

R. Vigneri, et al., "Insulin and its analogs: actions via insulin and IGF receptors", Acta Diabetol, 2010, pp. 271-278, vol. 47, No. 4.

NCBI, "insulin preproprotein [*Homo sapiens*]", NCBI Reference Sequence: NP_000198.1, Feb. 17, 2013, [online]<http://www.ncbi.nlm.nih.gov/protein/4557671?sat=17&satkey=22757282> retrieved on Mar. 31, 2014.

Senshang Lin, et al., "Comparative Pharmacokinetic and Pharmacodynamic Studies of Human Insulin and Analogues in Chronic Diabetic Yucatan Minipigs", The Journal of Pharmacology and Experimental Therapeutics, Apr. 13, 1998, pp. 959-966, vol. 286, No. 2.

Jens Brange, MSc et al., "Monomeric Insulins and Their Experimental and Clinical Implications", Diabetes Care, Sep. 1990, pp. 923-954, vol. 13, No. 9.

Ulla Ribel, et al., "Equivalent In Vivo Biological Activity of Insulin Analogues and Human Insulin Despite Different In Vitro Potencies", Diabetes, Sep. 1990, pp. 1033-1039, vol. 39.

International Searching Authority, International Search Report for PCT/KR2014/001593 dated May 22, 2014.

International Searching Authority, Written Opinion of the International Search Authority for PCT/KR2014/001593 dated May 22, 2014.

Chile Patent Office, Communication dated Aug. 22, 2016, issued in corresponding Chilean Application No. 2015-002330.

European Patent Office; Communication dated Nov. 30, 2016, in counterpart European Application No. 14757629.2.

Colombian Patent Office; Communication dated Nov. 8, 2016, in counterpart Columbian application No. 15227010.

European Patent Office; Communication dated May 10, 2017, in counterpart European application No. 14757629.2.

Chilean Patent Office, Communication dated Jul. 13, 2017 by the Chilean Patent Office in counterpart Chilean Patent Application No. 201601844.

European Patent Office, Communication dated Sep. 20, 2017 by the European Patent Office in counterpart European Patent Application No. EP 15 73 7856.

Authier F. et al. (1998) "Uptake and Metabolic Fate of [His$^{48}$, His$^{B4}$, Glu$^{B10}$, His$^{B27}$] Infulin in Rat Liver In Vivo," Biochem J. 332;421-30.

Duckworth, W.C. et al. (Oct. 1998). "Insulin Degradation: Process and Potential," Endocr Rev. 19(5):608-24.

Valera, M. M. et al. (Dec. 2003). "Insulin Clearance in Obesity," J Am Coll Ntur. 22(6):487-93, Abstract Only.

United States Patent and Trademark Office communication dated Sep. 14, 2017 in counterpart U.S. Appl. No. 15/250,459.

UniProtKB A6XGL2, pp. 1-5. Integrated in UniProtKB/TrEMBL Aug. 21, 2007.

Keller, D. et al. (2001). "Flexibility and Bioactivity of Insulin: an NMR Investigation of the Solution Structure and Folding of an Unusually Flexible Human Insulin Mutant with Increased Biological Activity," Biochemistry 40(35):10732-10740.

(56) References Cited

OTHER PUBLICATIONS

NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=seqview, last visited on Jun. 20, 2017.
NCBI, Genbank AKI70564.1 (Jun. 1, 2015). "INS, Partial [synthetic construct]" located at <https://www.ncbi.nlm.nih.gov/protein/Aki70564.1?report=gpwithparts&log$=seqview> last visited on Jun. 20, 2017.
NCBI, Genbank NM_001291897.1, (May 13, 2015). "*Homo sapiens* Insulin (INS), Transcript Variant 4, mRNA," located at <https://www.ncbi.nlm.nih.gov/nuccore/NM-001291897.1?report=gpwithparts&log$=seqview&sat=4&satkey=139944924>, last visited on Jun. 20, 2017, 4 pages.
Yampolsky et al., "The Exchangeability of Amino Acids in Proteins," Genetics, 170: 1459-1472, 2005.
Rudinger J., "Characteristics of the Amino Acids as Components of a Peptide Hormone Sequence," Peptide Hormones, J.A. Parsons Edition, University Park Press, Jun. 1976, pp. 1-7. (8 pages total).
"Designing Custom Peptides," from Sigma Genosys, pp. 1-2. Accessed Dec. 16, 2004.
Schinzel R., Drueckes P., "The Phosphate Recognition Site of *Escherichia coli* Maltodextrin Phosphorylase," FEBS, Jul. 1991. 286(1,2): 125-128.
Berendsen HJC, "A Glimpse of the Holy Grail?" Science, 1998, 282: 642-643.
Voet D, Voet JG, Biochemistry, Second Edition, John Wiley & Sons, Inc., 1995, pp. 235-241. (9 pages).
Ngo J.T., Marks J, Karplus M., "Computational Complexity, Protein Structure Prediction, and the Levinthal Paradox," The Protein Folding Problem and Teritary Structure Prediction, K. Merc Jr. and S. Le Grand Edition, 1994, pp. 491-495.
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.
Betts et al., "Amino Acid Properties and Consequences of Substitutions," Bioinformatics for Geneticists, Chapter 14, John Wiley & Sons, Ltd., 2003, pp. 289-316.
Jørgensen, A. et al (Apr. 1996). "Solution Structure of the Superactive Monomeric Des-[Phe(B25)] Human Insulin Mutant: Elucidation of the Structural Basis for the Monomerizatio of Des-[Phe(B25)] Insulin and the Dimerization of Native Insulin." 257(3):684-699.
Uhlman, E. et al. (Jun. 1990). "Antisense Oligonucleotides: A New Therapeutic Principle," Chemical Reviews 90(4):543-584.
United States Patent and Trademark Office Communication dated Sep. 8, 2017 in counterpart U.S. Appl. No. 15/313,501.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].
International Searching Authority, Written Opinion of PCT/KR2015/005455 dated Aug. 24, 2015 [PCT/ISA/237].
Colombian Patent Office; Communication dated Aug. 24, 2017, in counterpart Colombian application No. 15227010.
Taiwanese Intellectual Property Office; Communication dated Sep. 11, 2017 in counterpart application No. 103106674.
Intellectual Property Office of Singapore, Communication dated Oct. 3, 2017 in counterpart application No. 11201609564T.
European Patent Office, Communication dated Nov. 10, 2017 in counterpart application No. 15799334.6.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.
European Patent Office; Communication dated Nov. 17, 2017 in counterpart application No. 15799077.1.
United States Patent and Trademark Office; Notice of Allowance dated Feb. 26, 2018 in U.S. Appl. No. 15/250,459.
United States Patent and Trademark Office; Non-Final Office Action dated Jan. 16, 2018 in U.S. Appl. No. 15/113,027.
United States Patent and Trademark Office; Final Rejection dated Mar. 8, 2018 in U.S. Appl. No. 15/313,501.
Japanese Patent Office; Communication dated Jan. 16, 2018 in counterpart Japanese application No. 2015-559199.
Saudi Arabian Patent Office, Communication dated Apr. 30, 2016 issued in corresponding Application No. 515360933, with English translation.
Intellectual Property Office of Singapore; Communication dated Jan. 26, 2018 in counterpart Singaporean application No. 11201609872Y.
United States Patent and Trademark Office; Non-Final Office Action dated Apr. 17, 2018 in co-pending U.S. Appl. No. 15/315,020.
Colombian Patent and Trademark Office; communication dated Feb. 16, 2018, in Colombian application No. NC2016/0004794.
Kristensen et al., "Alanine Scanning Mutagenesis of Insulin," J. Biol. Chem. 272:12978-12983 (1997).
Chen et al., "Four new monomeric insulins obtained by alanine scanning the dimer-forming surface of the insulin molecule," Protein Eng'g 13:779-782 (2000).
Nakagawa et al., "Chiral Mutagenesis of Insulin, Contribution of the B20-B23 p-turn to activity and stability," J. Biol. Chem. 281: 22386-22396, (2006).
Chu et al., "The A14 Position of Insulin Tolerates Considerable Structural Alterations with Modest Effects on the Biological Behavior of the Hormone," J. Prot. Chem. 11:571-577 (1992).
Mohan, "Which insulin to use? Human or animal?," Curr. Sci. 83:1544-1547 (2002).
Chinese Patent and Trademark Office; communication dated Mar. 1, 2018, in Chinese Patent Application No. 201480006998.4.
Japanese Patent Office; Communication dated Sep. 11, 2018 in counterpart application No. 2015-559199.
Intellectual Property Office of the Dominican Republic; Communication dated Jul. 26, 2018 in counterpart application No. P2016-176.
Chilean Patent Office; Communication dated May 29, 2018 issued in counterpart Chilean Application No. 201603069.
United States Patent and Trademark Office; Final Rejection dated Jul. 17, 2018 in counterpart U.S. Appl. No. 15/113,027.
Glendorf et al., "Engineering of Insulin Receptor Isoform-Selective Insulin Analogues", PLOS One, vol. 6, Issue 5, e20288, May 2011, 7 pages total.
Chilean Patent Office; Communication dated Nov. 14, 2018 issued in copending application No. 201603069.
Japanese Patent Office: Communication dated Nov. 13, 2018 in counterpart application No. 2016-564933.
Ukraine Patent Office; Communication dated Jul. 2, 2018 in counterpart application No. 12469/3A/18.
Intellectual Property Office of Taiwan; Communication dated Jun. 29, 2018 in counterpart application No. 106143717.
Pocai, "Unraveling oxyntomodulin, GLP1's enigmatic brother", Journal of Endocrinology, vol. 215, No. 3, pp. 335-346, Sep. 27, 2012.
Hinds et al., "Effects of PEG conjugation on insulin properties", Advanced Drug Delivery Reviews, vol. 54, No. 4, pp. 505-530, 2002.
Thibaudeau et al., "Synthesis and Evaluation of Insulin—Human Serum Albumin Conjugates", Bioconjugate Chemistry, American Chemical Society, vol. 16, No. 4, pp. 1000-1008, Jun. 25, 2005.

\* cited by examiner

[FIG. 1]
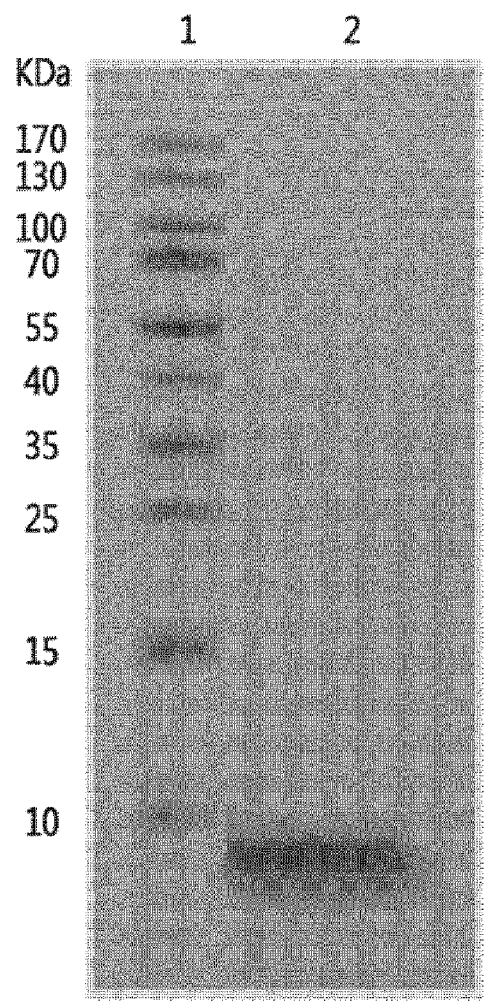
1. Size Marker
2. Insulin Analog

[FIG. 2]
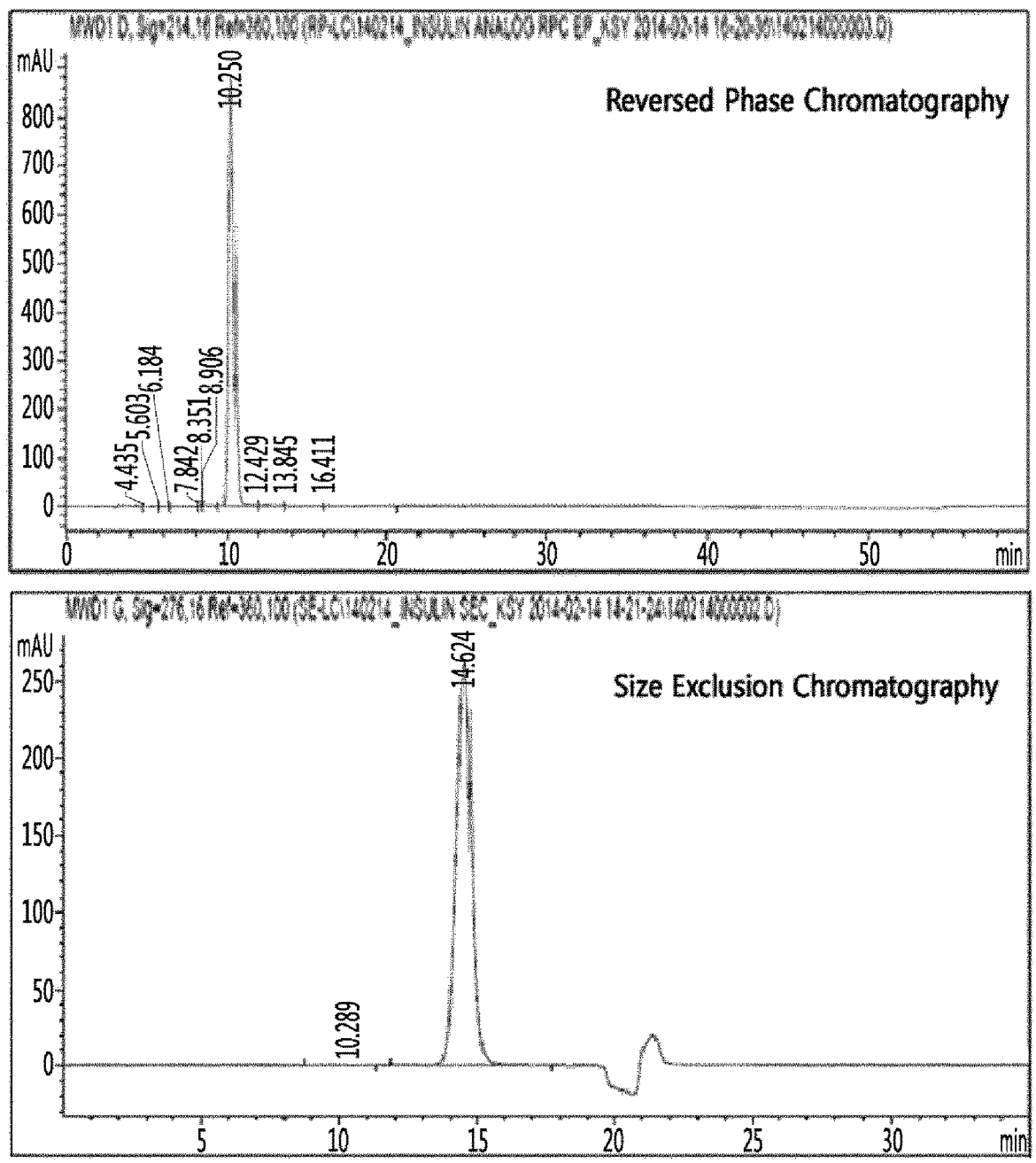

[FIG. 3]
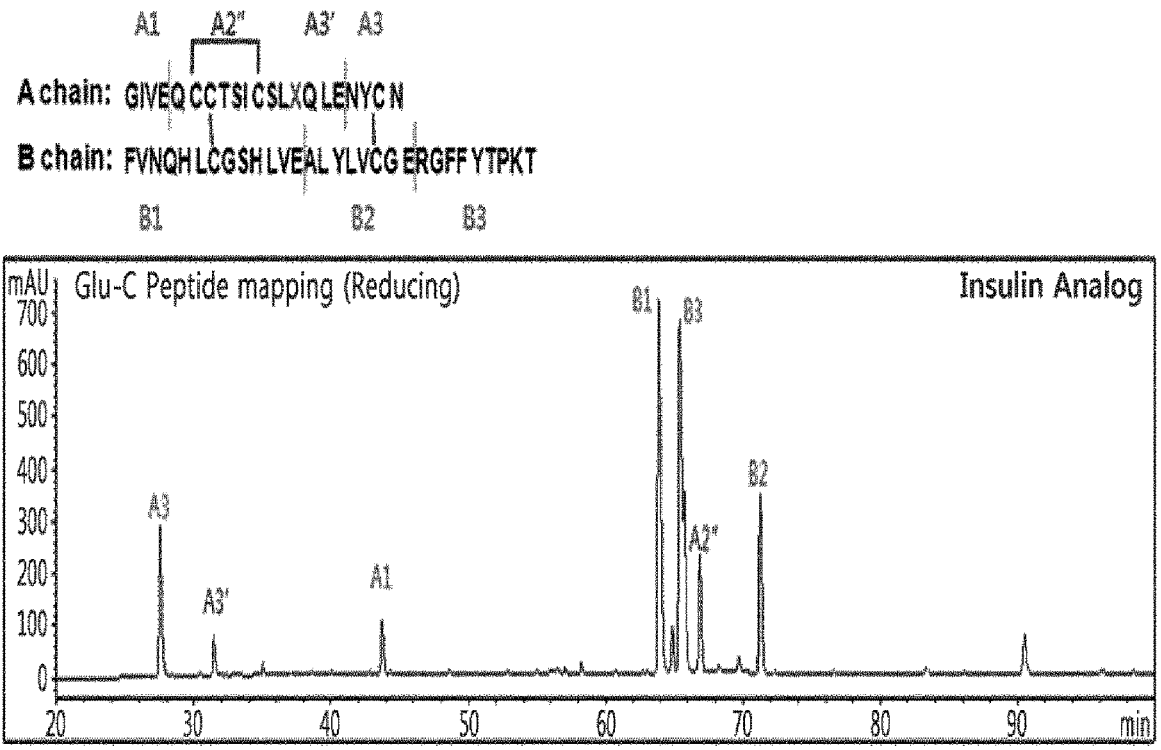
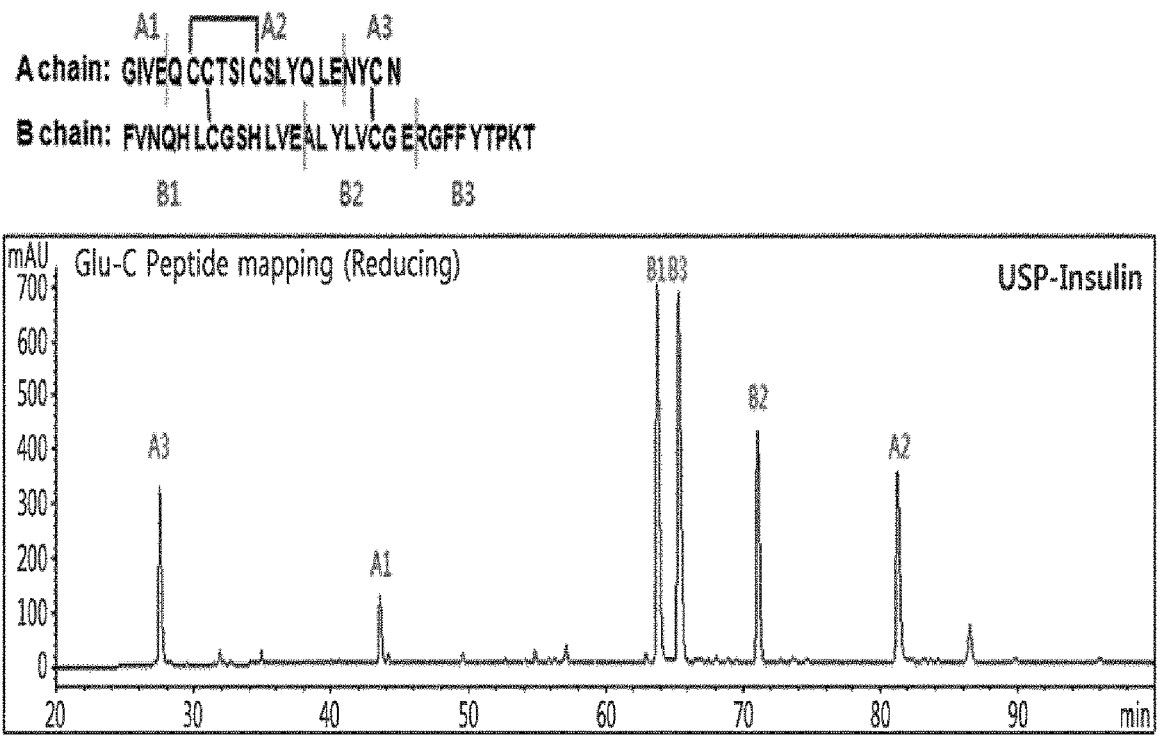

SEQUENCE LISTING

```
<160> NUMBER OF SEQ ID NOS: 24

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Insulin A-chain
<220> FEATURE:
<221> NAME/KEY: VARIANT
<222> LOCATION: 1
<223> OTHER INFORMATION: Xaa = Ala, Gly, Gln, His, Glu, or Asn
<220> FEATURE:
<221> NAME/KEY: VARIANT
<222> LOCATION: 5
<223> OTHER INFORMATION: Xaa = Ala, Glu, Gln, His, or Asn
<220> FEATURE:
<221> NAME/KEY: VARIANT
<222> LOCATION: 12
<223> OTHER INFORMATION: Xaa = Ala, Ser, Gln, Glu, His, or Asn
<220> FEATURE:
<221> NAME/KEY: VARIANT
<222> LOCATION: 14
```

```
<223> OTHER INFORMATION: Xaa = Ala, Tyr, Glu, His, Lys, Asp, or Asn
<220> FEATURE:
<221> NAME/KEY: VARIANT
<222> LOCATION: 16
<223> OTHER INFORMATION: Xaa = Ala, Leu, Tyr, His, Glu, or Asn
<220> FEATURE:
<221> NAME/KEY: VARIANT
<222> LOCATION: 19
<223> OTHER INFORMATION: Xaa = Ala, Tyr, Ser, Glu, His, or Asn
<220> FEATURE:
<221> NAME/KEY: VARIANT
<222> LOCATION: 21
<223> OTHER INFORMATION: Xaa = Asn, Gly, His, or Ala

<400> SEQUENCE: 3

Xaa Ile Val Glu Xaa Cys Cys Thr Ser Ile Cys Xaa Leu Xaa Gln Xaa
 1               5                  10                  15

Glu Asn Xaa Cys Xaa
            20

<210> SEQ ID NO 4
<211> LENGTH: 30
<212> TYPE: PRT
<213> ORGANISM: Artificial Sequence
<220> FEATURE:
<223> OTHER INFORMATION: Insulin B-chain
<220> FEATURE:
<221> NAME/KEY: VARIANT
<222> LOCATION: 16
<223> OTHER INFORMATION: Xaa = Tyr, Glu, or Asp, or is absent
<220> FEATURE:
<221> NAME/KEY: VARIANT
<222> LOCATION: 25
<223> OTHER INFORMATION: Xaa = Phe, or is absent
<220> FEATURE:
<221> NAME/KEY: VARIANT
<222> LOCATION: 27
<223> OTHER INFORMATION: Xaa = Thr, or is absent
<220> FEATURE:
<221> NAME/KEY: VARIANT
<222> LOCATION: 28
<223> OTHER INFORMATION: Xaa = Pro, Glu, or Asp, or is absent

<400> SEQUENCE: 4

Phe Val Asn Gln His Leu Cys Gly Ser His Leu Val Glu Ala Leu Xaa
 1               5                  10                  15

Leu Val Cys Gly Glu Arg Gly Phe Xaa Tyr Xaa Xaa Lys Thr
            20                  25                  30

<210> SEQ ID NO 5
<211> LENGTH: 37
<212> TYPE: DNA
<213> ORGANISM: Artificial Sequence
<220> FEATURE:
<223> OTHER INFORMATION: Primer

<400> SEQUENCE: 5
ccagcatctg ctccctcgaa cagctggaga actactg                           37

<210> SEQ ID NO 6
<211> LENGTH: 37
<212> TYPE: DNA
<213> ORGANISM: Artificial Sequence
<220> FEATURE:
<223> OTHER INFORMATION: Primer

<400> SEQUENCE: 6
cagtagttct ccagctgttc gagggagcag atgctgg                           37
```

```
<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
cagcatctgc tccctcaacc agctggagaa ctac                        34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gtagttctcc agctggttga gggagcagat gctg                        34

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gcggggaacg aggcttctac acacccaaga cccg                        34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
cgggtcttgg gtgtgtagaa gcctcgttcc ccgc                        34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
cagcatctgc tccctcgccc agctggagaa ctac                        34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gtagttctcc agctgggcga gggagcagat gctg                        34

<210> SEQ ID NO 13
<211> LENGTH: 34
<212> TYPE: DNA
<213> ORGANISM: Artificial Sequence
<220> FEATURE:
<223> OTHER INFORMATION: Primer
```

```
<400> SEQUENCE: 13
ctggtggaag ctctcgagct agtgtgcggg gaac                              34

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
gttccccgca cactagctcg agagcttcca ccag                              34

<210> SEQ ID NO 15
<211> LENGTH: 261
<212> TYPE: DNA
<213> ORGANISM: Artificial Sequence
<220> FEATURE:
<223> OTHER INFORMATION: Insulin Analog 1

<400> SEQUENCE: 15
ttcgttaacc aaacacttgtg tggctcacac ctggtggaag ctctctacct agtgtgcggg    60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga gcgtggcat tgtggaacaa tgctgtacca gcatctgctc cctcgaacag    240
ctggagaact actgcaactg a                                            261

<210> SEQ ID NO 16
<211> LENGTH: 86
<212> TYPE: PRT
<213> ORGANISM: Artificial Sequence
<220> FEATURE:
<223> OTHER INFORMATION: Insulin Analog 1

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn
                85

<210> SEQ ID NO 17
<211> LENGTH: 261
<212> TYPE: DNA
<213> ORGANISM: Artificial Sequence
<220> FEATURE:
<223> OTHER INFORMATION: Insulin Analog 2

<400> SEQUENCE: 17
ttcgttaacc aaacacttgtg tggctcacac ctggtggaag ctctctacct agtgtgcggg    60
gaacgaggct tcttctacac acccaagacc cgccggagg cagaggacct gcaggtgggg     120
caggtggagc tgggcggggg ccctggtgca ggcagcctgc agcccttggc cctggagggg    180
```
tccctgcaga agcgtggcat tgtggaacaa tgctgtacca gcatctgctc cctcaaccag    240
ctggagaact actgcaactg a                                              261

<210> SEQ ID NO 18
<211> LENGTH: 86
<212> TYPE: PRT
<213> ORGANISM: Artificial Sequence
<220> FEATURE:
<223> OTHER INFORMATION: Insulin Analog 2

<400> SEQUENCE: 18

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Asn Gln
65                  70                  75                  80

Leu Glu Asn Tyr Cys Asn
                85

<210> SEQ ID NO 19
<211> LENGTH: 258
<212> TYPE: DNA
<213> ORGANISM: Artificial Sequence
<220> FEATURE:
<223> OTHER INFORMATION: Insulin Analog 3

<400> SEQUENCE: 19
ttcgttaacc aaacacttgtg tggctcacac ctggtggaag ctctctacct agtgtgcggg     60
gaacgaggct tctacacacc caagacccgc cgggaggcag aggacctgca ggtggggcag    120
gtggagctgg gcggggggccc tggtgcaggc agcctgcagc ccttggccct ggaggggtcc   180
ctgcagaagc gtggcattgt ggaacaatgc tgtaccagca tctgctccct cgaacagctg    240
gagaactact gcaactga                                                  258

<210> SEQ ID NO 20
<211> LENGTH: 85
<212> TYPE: PRT
<213> ORGANISM: Artificial Sequence
<220> FEATURE:
<223> OTHER INFORMATION: Insulin Analog 3

<400> SEQUENCE: 20

Phe Val Asn Gln His Leu Cys Gly Ser His Leu Val Glu Ala Leu Tyr
1               5                  10                  15

Leu Val Cys Gly Glu Arg Gly Phe Tyr Thr Pro Lys Thr Arg Arg Glu
            20                  25                  30

Ala Glu Asp Leu Gln Val Gly Gln Val Glu Leu Gly Gly Gly Pro Gly
        35                  40                  45

Ala Gly Ser Leu Gln Pro Leu Ala Leu Glu Gly Ser Leu Gln Lys Arg
    50                  55                  60

Gly Ile Val Glu Gln Cys Cys Thr Ser Ile Cys Ser Leu Glu Gln Leu
65                  70                  75                  80

Glu Asn Tyr Cys Asn

<210> SEQ ID NO 21
<211> LENGTH: 258
<212> TYPE: DNA
<213> ORGANISM: Artificial Sequence
<220> FEATURE:
<223> OTHER INFORMATION: Insulin Analog 4

<400> SEQUENCE: 21

```
ttcgttaacc aacacttgtg tggctcacac ctggtggaag ctctcgagct agtgtgcggg    60
gaacgaggct tctacacacc caagacccgc cgggaggcag aggacctgca ggtggggcag   120
gtggagctgg cgggggcccc tggtgcaggc agcctgcagc ccttggccct ggaggggtcc   180
ctgcagaagc gtggcattgt gaacaatgc tgtaccagca tctgctccct cgcccagctg   240
gagaactact gcaactga                                                  258
```

<210> SEQ ID NO 22
<211> LENGTH: 85
<212> TYPE: PRT
<213> ORGANISM: Artificial Sequence
<220> FEATURE:
<223> OTHER INFORMATION: Insulin Analog 4

<400> SEQUENCE: 22

```
Phe Val Asn Gln His Leu Cys Gly Ser His Leu Val Glu Ala Leu Glu
1               5                   10                  15

Leu Val Cys Gly Glu Arg Gly Phe Tyr Thr Pro Lys Thr Arg Arg Glu
            20                  25                  30

Ala Glu Asp Leu Gln Val Gly Gln Val Glu Leu Gly Gly Gly Pro Gly
        35                  40                  45

Ala Gly Ser Leu Gln Pro Leu Ala Leu Glu Gly Ser Leu Gln Lys Arg
    50                  55                  60

Gly Ile Val Glu Gln Cys Cys Thr Ser Ile Cys Ser Leu Ala Gln Leu
65                  70                  75                  80

Glu Asn Tyr Cys Asn
            85
```

<210> SEQ ID NO 23
<211> LENGTH: 30
<212> TYPE: DNA
<213> ORGANISM: Artificial Sequence
<220> FEATURE:
<223> OTHER INFORMATION: N-terminal fusion partner

<400> SEQUENCE: 23

```
atggcaacaa catcaacagc aactacgcgt                                     30
```

<210> SEQ ID NO 24
<211> LENGTH: 10
<212> TYPE: PRT
<213> ORGANISM: Artificial Sequence
<220> FEATURE:
<223> OTHER INFORMATION: N-terminal fusion partner

<400> SEQUENCE: 24

```
Met Ala Thr Thr Ser Thr Ala Thr Thr Arg
1               5                   10
```

INSULIN ANALOGS AND USE THEREOF

CROSS-REFERENCE TO RELATED APPLICATIONS

This application is a Rule 53(b) Continuation Application of U.S. application Ser. No. 15/250,459 filed Aug. 29, 2016, claiming priority based on Korean Patent Application No. 10-2015-0121819 filed Aug. 28, 2015, the contents of all of which are incorporated herein by reference in their entirety.

SEQUENCE LISTING

The content of the Sequence Listing in computer readable form submitted in application Ser. No. 15/250,459 is incorporated herein by reference.

TECHNICAL FIELD

The present invention relates to a novel insulin analog, and more specifically, to an insulin analog with an improved in vitro effect compared with native insulin, and a use thereof.

BACKGROUND ART

Insulin is a blood glucose level-controlling hormone secreted by the pancreas, and serves to transport excess glucose in the blood to cells, thereby supplying an energy source and maintaining a normal glucose level. However, diabetic patients cannot maintain normal insulin functions due to insulin deficiency, insulin resistance, and loss of beta-cell function. As a result, diabetic patients cannot utilize the glucose in the blood as an energy source, but show symptoms of hyperglycemia with a high glucose level and excrete the glucose in the urine, which cause of various complications. Accordingly, those diabetic patients who have abnormalities in insulin secretion (type I) or insulin resistance (type II) essentially require insulin treatment, and by insulin administration, they can keep their blood glucose levels normal.

Human insulin consists of two polypeptide chains, i.e., the A-chain and the B-chain, which respectively include 21- and 30 amino acids, connected with each other by two disulfide bonds. Since insulin has an extremely short in vivo half-life, as is the case with other protein and peptide hormones, it is unable to show a sustained therapeutic effect, and thus has a problem in that it must be administered continuously and repeatedly to exert its effect. The frequent administration of insulin causes severe pain and discomfort to patients, and thus there is a need to improve the administration from the aspects of patient compliance, safety, and convenience.

Accordingly, studies have focused on the development of various protein formulations, chemical conjugates, etc. for improving the therapeutic effects as well as the quality of patients' lives by reducing the frequency of administration through the increase of the in vivo half-life of these protein drugs such as insulin.

Insulin is known to remove blood glucose by binding to insulin receptors and the effect of insulin can be controlled by altering the sequence of native insulin. The in vivo effect of insulin can be controlled by substitution of amino acid(s) of insulin with different amino acid(s) or by deletion of specific amino acid(s) of insulin. Since insulin derivatives with high activity can exert effects equivalent to or better than those of native insulin, even in a small amount, they may thus be very desirable from the therapeutic point of view. In particular, amino acid substitutions in the A-chain and/or the B-chain contained in insulin have been broadly studied from the aspect of a pharmacokinetic effect of insulin action after subcutaneous injection.

Under these circumstances, the present inventors have intensively studied to improve the effect of insulin action, and as a result, they have discovered that the insulin analogs with modification(s) in particular amino acid residue(s) in the A-chain and/or the B-chain of insulin exhibit a markedly improved in vitro effect compared to that of native insulin, and that they can thus be effectively used for treating diabetes, thereby completing the present invention.

DISCLOSURE

Technical Problem

An object of the present invention is to provide a novel insulin analog, and specifically an insulin analog with an improved in vitro effect compared with that of native insulin.

Another object of the present invention is to provide a pharmaceutical composition for treating diabetes containing the insulin analog as an active ingredient.

A further object of the present invention is to provide a method for treating diabetes including administering the insulin analog or a pharmaceutical composition containing the insulin analog as an active ingredient to a subject in need thereof.

Technical Solution

In order to achieve the above objects, in an aspect, the present invention provides an insulin analog which includes the A-chain of SEQ ID NO: 3 represented by the following General Formula 1 and the B-chain of SEQ ID NO: 4 represented by the following General Formula 2.

```
General Formula 1
                                      (SEQ ID NO: 3)
Xaa1-Ile-Val-Glu-Xaa2-Cys-Cys-Thr-Ser-Ile-Cys- Xaa3-Leu-Xaa4-Gln-Xaa5-Glu-Asn-Xaa6-Cys-Xaa7
```

In the above General Formula 1,

Xaa1 is alanine, glycine, glutamine, histidine, glutamic acid, or asparagine;

Xaa2 is alanine, glutamic acid, glutamine, histidine, or asparagine;

Xaa3 is alanine, serine, glutamine, glutamic acid, histidine, or asparagine;

Xaa4 is alanine, tyrosine, glutamic acid, histidine, lysine, aspartic acid, or asparagine;

Xaa5 is alanine, leucine, tyrosine, histidine, glutamic acid, or asparagine;

Xaa6 is alanine, tyrosine, serine, glutamic acid, histidine, or asparagine; and

Xaa7 is asparagine, glycine, histidine, or alanine.

```
General Formula 2
                                      (SEQ ID NO: 4)
Phe-Val-Asn-Gln-His-Leu-Cys-Gly-Ser-His-Leu-Val- Glu-Ala-Leu-Xaa8-Leu-Val-Cys-Gly-Glu-Arg-Gly-Phe- Xaa9-Tyr-Xaa10-Xaa11-Lys-Thr
```

In the above General Formula 2,

Xaa8 is tyrosine, glutamic acid, or aspartic acid, or is absent;

Xaa9 is phenylalanine, or is absent;

Xaa10 is threonine, or is absent; and

Xaa11 is proline, glutamic acid, or aspartic acid, or is absent;

(with the proviso that the peptides comprising the A-chain of SEQ ID NO: 1 and the B-chain of SEQ ID NO: 2 is excluded).

In a more specific exemplary embodiment, the insulin analog is characterized in that it includes an A-chain of General Formula 1 and a B-chain, wherein, in the B-chain of SEQ ID NO: 4, Xaa8 is tyrosine, Xaa9 is absent, and Xaa10 is threonine.

The insulin analog is characterized in that it includes an A-chain of General Formula 1 and a B-chain, wherein, in the B-chain of SEQ ID NO: 4, Xaa8 is tyrosine, Xaa9 is phenylalanine, and Xaa10 is absent.

In another exemplary embodiment, the insulin analog is characterized in that, in the A-chain of SEQ ID NO: 3, Xaa1 is glycine, Xaa2 is glutamine, Xaa3 is serine, Xaa4 is glutamic acid, Xaa5 is leucine, Xaa6 is tyrosine, and Xaa7 is asparagine, and in the B-chain of SEQ ID NO: 4, Xaa8 is tyrosine, Xaa9 is phenylalanine, Xaa10 is threonine, and Xaa11 is proline.

In still another exemplary embodiment, the insulin analog is characterized in that, in the A-chain of SEQ ID NO: 3, Xaa1 is glycine, Xaa2 is glutamine, Xaa3 is serine, Xaa4 is asparagine, Xaa5 is leucine, Xaa6 is tyrosine, and Xaa7 is asparagine, and in the B-chain of SEQ ID NO: 4, Xaa8 is tyrosine, Xaa9 is phenylalanine, Xaa10 is threonine, and Xaa11 is proline.

In still another exemplary embodiment, the insulin analog is characterized in that, in the A-chain of SEQ ID NO: 3, Xaa1 is glycine, Xaa2 is glutamine, Xaa3 is serine, Xaa4 is glutamic acid, Xaa5 is leucine, Xaa6 is tyrosine, and Xaa7 is asparagine, and in the B-chain of SEQ ID NO: 4, Xaa8 is tyrosine, Xaa9 is absent, Xaa10 is threonine, and Xaa11 is proline.

In still another exemplary embodiment, the insulin analog is characterized in that, in the A-chain of SEQ ID NO: 3, Xaa1 is glycine, Xaa2 is glutamine, Xaa3 is serine, Xaa4 is alanine, Xaa5 is leucine, Xaa6 is tyrosine, and Xaa7 is asparagine, and in the B-chain of SEQ ID NO: 4, Xaa8 is glutamic acid, Xaa9 is absent, Xaa10 is threonine, and Xaa11 is proline.

In still another exemplary embodiment, the insulin analog according to the present invention is characterized in that, in the A-chain of SEQ ID NO: 3, Xaa4 is glutamic acid, and, in the B-chain of SEQ ID NO: 4, Xaa9 is phenylalanine; or in the A-chain of SEQ ID NO: 3, Xaa4 is asparagine, and, in the B-chain of SEQ ID NO: 4, Xaa9 is phenylalanine; or in the A-chain of SEQ ID NO: 3, Xaa4 is glutamic acid, and, in the B-chain of SEQ ID NO: 4, Xaa9 is absent; or in the A-chain of SEQ ID NO: 3, Xaa4 is alanine, and, in the B-chain of SEQ ID NO: 4, Xaa8 is glutamic acid and Xaa9 is absent, but is not limited thereto.

In still another exemplary embodiment, the insulin analog according to the present invention includes an amino acid sequence represented by SEQ ID NO: 16, 18, 20, or 22.

In another aspect, the present invention provides a nucleic acid encoding the insulin analog.

In an exemplary embodiment, the nucleic acid according to the present invention includes nucleotide sequences selected from the group consisting of SEQ ID NOS: 15, 17, 19, and 21.

In still another aspect, the present invention provides a recombinant expression vector including the nucleic acid.

In still another aspect, the present invention provides a transformant which is transformed with the recombinant expression vector.

In still another aspect, the present invention provides a method for preparing the insulin analog including:

a) preparing a recombinant expression vector including a nucleic acid encoding the insulin analog peptide;

b) transforming the recombinant expression vector into a host cell and obtaining a transformant therefrom;

c) culturing the transformant and expressing the insulin analog peptide; and d) isolating and purifying the expressed insulin analog peptide.

In still another aspect, the present invention provides a pharmaceutical composition for treating diabetes containing the insulin analog as an active ingredient and a pharmaceutically acceptable carrier.

The present invention will be described in greater detail hereinbelow.

Meanwhile, each of the explanations and exemplary embodiments disclosed herein can be applied to other explanations and exemplary embodiments. That is, all possible combinations of various elements disclosed herein belong to the scope of the present invention. Additionally, the scope of the present invention should not be limited by the specific descriptions provided hereinbelow.

The present invention relates to a novel insulin, and specifically an insulin analog with an improved in vitro effect compared with that of native insulin.

As used herein, the term "insulin analog" refers to a modified analog of native insulin prepared via modification of a part of the amino acid(s) of native insulin in the form of insertion, deletion, or substitution, and in particular, it includes various insulin analogs of native insulin with an improved in vitro effect compared with that of native insulin.

Native insulin is a hormone secreted by the pancreas and generally plays a role in promoting intracellular glucose absorption and inhibiting fat breakdown, thereby controlling in vivo blood glucose levels. Insulin is generated from the processing of its precursor, proinsulin, which does not have the function of controlling blood glucose levels. Insulin is composed of two polypeptide chains, i.e., the A-chain and the B-chain, which include 21 and 30 amino acids, respectively, and are interlinked by a disulfide bridge. Each of the A-chain and the B-chain may include the amino acid sequences represented by SEQ ID NO: 1 and SEQ ID NO: 2 shown below.

A-chain:
(SEQ ID NO: 1)
Gly-Ile-Val-Glu-Gln-Cys-Cys-Thr-Ser-Ile-Cys-Ser-

Leu-Tyr-Gln-Leu-Glu-Asn-Tyr-Cys-Asn

B-chain:
(SEQ ID NO: 2)
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The insulin according to the present invention refers to insulin analogs prepared by genetic recombination technology, but the insulin is not limited thereto and includes all insulin with an improved in vitro effect compared with that of native insulin. Preferably, the insulin of the present invention includes inverted insulin, insulin variants, insulin fragments, etc. The insulin can be prepared not only by a recombinant method but also by a solid phase synthesis, and the preparation method is not limited thereto.

These insulin analogs, being peptides having an in vivo blood glucose level-controlling capability equivalent or corresponding to that of native insulin, include all of insulin agonists, insulin derivatives, insulin fragments, insulin variants, etc.

As used herein, the term "insulin agonist" refers to a material which can bind to an in vivo receptor of insulin regardless of the structure of insulin and thereby exhibit a biological activity equivalent to that of insulin.

As used herein, the term "insulin derivative" may refer to a peptide which has a homology to each of the amino acid sequences of the A-chain and the B-chain of native insulin and is in the form having an in vivo blood glucose level-controlling capability, where a part of the groups in an amino acid residue is modified by chemical substitution (e.g., alpha-methylation, alpha-hydroxylation), deletion (e.g., deamination), or modification (e.g., N-methylation).

Additionally, as used herein, the term "insulin derivative" may refer to a peptide mimic and a low or high molecular weight compound which can control in vivo blood glucose levels by binding to an insulin receptor, although there is no sequence homology to the amino acid sequence of native insulin.

As used herein, the term "insulin fragment" refers to a form of insulin in which at least one amino acid is inserted or deleted, and the amino acid inserted may be one that is not present in nature (e.g., D-type amino acid), and the insulin fragment has an in vivo blood glucose level-controlling capability.

As used herein, the term "insulin variant" refers to a peptide which has a difference in at least one amino acid sequence from that of insulin, and the peptide also has the in vivo blood glucose level-controlling capability.

The methods used in preparing insulin agonists, derivatives, fragments, and variants may be used independently or in combination. For example, those peptides having the in vivo blood glucose level-controlling capability, which have a difference in at least one amino acid sequence, and in which the amino acid residue in the N-terminus is deaminated, may be included in the scope of the present invention.

The insulin analog according to the present invention exclusively includes any peptide with an improved in vitro effect compared with that of native insulin by introducing substitution, insertion, or deletion of amino acid(s), or a post-translational modification (e.g., methylation, acylation, ubiquitination, and intermolecular covalent bond) in the amino acid sequences (SEQ ID NOS: 1 and 2) of the A-chain and the B-chain of native insulin. For the substitution or insertion of the amino acid(s), not only the 20 amino acids conventionally observed in human proteins but also atypical or unnatural amino acids may be used. The atypical amino acids may be commercially obtained from Sigma-Aldrich, ChemPep, Genzymepharmaceuticals, etc. The peptides containing these amino acids and typical peptide sequences may be synthesized by or purchased from commercial peptide synthesis companies, such as American Peptide Company, Bachem (USA), and Anygen (Korea).

Specifically, the insulin analogs according to the present invention may be those which include a modification or deletion in particular amino acid residue(s) of the A-chain and the B-chain of native insulin, and preferably, may be those in which particular amino acid residue(s) of the A-chain of native insulin is(are) modified and particular amino acid residue(s) of the B-chain of native insulin is(are) modified and/or deleted.

Preferably, the insulin analogs of the present invention may be an analog in which the $14^{th}$ amino acid residue, tyrosine, in the amino acid sequence of the A-chain represented by SEQ ID NO: 1 is substituted with glutamic acid, asparagine, or alanine, or an analog in which the $16^{th}$ amino acid residue, tyrosine, is substituted with glutamic acid and/or the $25^{th}$ amino acid residue, phenylalanine, in the amino acid sequence of the B-chain represented by SEQ ID NO: 2 is deleted; or may include all of these.

More preferably, the insulin analogs of the present invention may be those which include the A-chain of SEQ ID NO: 3 represented by the following General Formula 1 and the B-chain of SEQ ID NO: 4 represented by the following General Formula 2.

```
General Formula 1
                                            (SEQ ID NO: 3)
Xaa1-Ile-Val-Glu-Xaa2-Cys-Cys-Thr-Ser-Ile-Cys- Xaa3-Leu-Xaa4-Gln-Xaa5-Glu-Asn-Xaa6-Cys-Xaa7
```

In the above General Formula 1, Xaa1 is alanine, glycine, glutamine, histidine, glutamic acid, or asparagine;

Xaa2 is alanine, glutamic acid, glutamine, histidine, or asparagine;

Xaa3 is alanine, serine, glutamine, glutamic acid, histidine, or asparagine;

Xaa4 is alanine, tyrosine, glutamic acid, histidine, lysine, aspartic acid, or asparagine;

Xaa5 is alanine, leucine, tyrosine, histidine, glutamic acid, or asparagine;

Xaa6 is alanine, tyrosine, serine, glutamic acid, histidine, or asparagine; and

Xaa7 is asparagine, glycine, histidine, or alanine.

```
General Formula 2
                                            (SEQ ID NO: 4)
Phe-Val-Asn-Gln-His-Leu-Cys-Gly-Ser-His-Leu-Val- Glu-Ala-Leu-Xaa8-Leu-Val-Cys-Gly-Glu-Arg-Gly-Phe- Xaa9-Tyr-Xaa10-Xaa11-Lys-Thr
```

In the above General Formula 2,

Xaa8 is tyrosine, glutamic acid, or aspartic acid, or is absent;

Xaa9 is phenylalanine, or is absent;

Xaa10 is threonine, or is absent; and

Xaa11 is proline, glutamic acid, or aspartic acid, or is absent; (wherein the peptides including the A-chain of SEQ ID NO: 1 and the B-chain of SEQ ID NO: 2 may be excluded).

In a more specific exemplary embodiment, the insulin analog may be an insulin analog, wherein, in General Formula 1, Xaa1 is glycine, Xaa2 is glutamine, Xaa3 is serine, Xaa4 is alanine, glutamic acid, or asparagine, Xaa5 is leucine, Xaa6 is tyrosine, and
Xaa7 is asparagine; and
in General Formula 2,
Xaa8 is tyrosine or glutamic acid,
Xaa9 is phenylalanine, or is absent,
Xaa10 is threonine, and
Xaa11 is proline, glutamic acid, or aspartic acid, or is absent, but is not limited thereto.

In another specific exemplary embodiment, the insulin analog may be an insulin analog, wherein, in General Formula 1,
Xaa1 is glycine,
Xaa2 is glutamine,
Xaa3 is serine,
Xaa4 is glutamic acid or asparagine,
Xaa5 is leucine,
Xaa6 is tyrosine, and
Xaa7 is asparagine; and
in General Formula 2,
Xaa8 is tyrosine,
Xaa9 is phenylalanine, or is absent,
Xaa10 is threonine, and
Xaa11 is proline, glutamic acid, or aspartic acid, or is absent,
but is not limited thereto.

In still another specific exemplary embodiment, the insulin analog may include an A-chain of General Formula 1 and a B-chain, wherein, in the B-chain of SEQ ID NO: 4, Xaa8 is tyrosine, Xaa9 is absent, Xaa10 is threonine, and Xaa11 is proline, glutamic acid, or aspartic acid, or is absent, but is not limited thereto.

The insulin analog may include an A-chain of General Formula 1 and a B-chain, wherein, in the B-chain of SEQ ID NO: 4, Xaa8 is tyrosine, Xaa9 is phenylalanine, Xaa10 is absent, and Xaa11 is proline, glutamic acid, or aspartic acid, or is absent, but is not limited thereto.

The insulin analog may be characterized in that, in the A-chain of SEQ ID NO: 3, Xaa1 is glycine, Xaa2 is glutamine, Xaa3 is serine, Xaa4 is glutamic acid, Xaa5 is leucine, Xaa6 is tyrosine, and Xaa7 is asparagine, and in the B-chain of SEQ ID NO: 4, Xaa8 is tyrosine, Xaa9 is phenylalanine, Xaa10 is threonine, and Xaa11 is proline, glutamic acid, or aspartic acid, or is absent, but is not limited thereto.

The insulin analog may be characterized in that, in the A-chain of SEQ ID NO: 3, Xaa1 is glycine, Xaa2 is glutamine, Xaa3 is serine, Xaa4 is asparagine, Xaa5 is leucine, Xaa6 is tyrosine, and Xaa7 is asparagine, and in the B-chain of SEQ ID NO: 4, Xaa8 is tyrosine, Xaa9 is phenylalanine, Xaa10 is threonine, and Xaa11 is proline, glutamic acid, or aspartic acid, or is absent, but is not limited thereto.

In still another specific exemplary embodiment, the insulin analog may be characterized in that, in the A-chain of SEQ ID NO: 3, Xaa1 is glycine, Xaa2 is glutamine, Xaa3 is serine, Xaa4 is glutamic acid, Xaa5 is leucine, Xaa6 is tyrosine, and Xaa7 is asparagine, and in the B-chain of SEQ ID NO: 4, Xaa8 is tyrosine, Xaa9 is absent, Xaa10 is threonine, and Xaa11 is proline, glutamic acid, or aspartic acid, or is absent, but is not limited thereto.

In still another specific exemplary embodiment, the insulin analog may be characterized in that, in the A-chain of SEQ ID NO: 3, Xaa1 is glycine, Xaa2 is glutamine, Xaa3 is serine, Xaa4 is alanine, Xaa5 is leucine, Xaa6 is tyrosine, and Xaa7 is asparagine, and in the B-chain of SEQ ID NO: 4, Xaa8 is glutamic acid, Xaa9 is absent, Xaa10 is threonine, and Xaa11 is proline, glutamic acid, or aspartic acid, or absent, but is not limited thereto.

In an exemplary embodiment, the insulin analogs of the present invention may include the following analogs:

i) insulin analog 1: A peptide in which the 14$^{th}$ amino acid residue in the amino acid sequence of the A-chain represented by SEQ ID NO: 3 is glutamic acid and the 25$^{th}$ amino acid residue in the amino acid sequence of the B-chain represented by SEQ ID NO: 4 is phenylalanine, having an amino acid sequence represented by SEQ ID NO: 16 which is encoded by a nucleic acid containing a nucleotide sequence represented by SEQ ID NO: 15.

ii) insulin analog 2: A peptide in which the 14$^{th}$ amino acid residue in the amino acid sequence of the A-chain represented by SEQ ID NO: 3 is asparagine and the 25$^{th}$ amino acid residue in the amino acid sequence of the B-chain represented by SEQ ID NO: 4 is phenylalanine, having an amino acid sequence represented by SEQ ID NO: 18 which is encoded by a nucleic acid containing a nucleotide sequence represented by SEQ ID NO: 17.

iii) insulin analog 3: A peptide in which the 14$^{th}$ amino acid residue in the amino acid sequence of the A-chain represented by SEQ ID NO: 3 is glutamic acid and the 25$^{th}$ amino acid residue in the amino acid sequence of the B-chain represented by SEQ ID NO: 4 is deleted, having an amino acid sequence represented by SEQ ID NO: 20 which is encoded by a nucleic acid containing a nucleotide sequence represented by SEQ ID NO: 19.

iv) insulin analog 4: A peptide in which the 14$^{th}$ amino acid residue in the amino acid sequence of the A-chain represented by SEQ ID NO: 3 is alanine and the 16$^{th}$ amino acid residue in the amino acid sequence of the B-chain represented by SEQ ID NO: 4 is glutamic acid, and the 25$^{th}$ amino acid residue is absent, having an amino acid sequence represented by SEQ ID NO: 22 which is encoded by a nucleic acid containing a nucleotide sequence represented by SEQ ID NO: 21.

As used herein, the term "in vitro effect" refers to glucose uptake by an insulin analog, and it is indicated by the measurement result of $EC_{50}$ on glucose uptake regarding mouse-derived 3T3-L1 cells differentiated into adipocytes.

In an exemplary embodiment, when the in vitro effect of insulin analogs 1 to 3 was measured, the insulin analog 1 showed a 238.4% increase of glucose uptake, the insulin analog 2 showed a 241.7% increase, and the insulin analog 3 showed a 705% increase compared with that of native insulin, respectively, thereby confirming that the insulin analogs according to the present invention exhibit a remarkable in vitro effect of a 2- to 7-fold increase compared with that of native insulin (Table 1).

In another aspect, the present invention provides nucleic acids encoding the above insulin analogs.

As used herein, the term "nucleic acid" refers to a deoxyribonucleotide (DNA) or ribonucleotide (RNA) including genomic DNA, cDNA, and RNA being transcribed therefrom, and a nucleotide as the basic constituting unit not only includes natural nucleotides but also includes analogues having modifications in a sugar or base (Scheit, Nucleotide Analogs, John Wiley, New York, 1980; Uhlman and Peyman, Chemical Reviews, 90: 543-584, 1990). The nucleic acid of the present invention may be isolated or prepared using standard technology in molecular biology. For example, the nucleic acid of the present invention may be prepared by PCR amplification using appropriate primer sequences based on the gene sequence of native insulin (NM_000207.2, NCBI), and may be prepared by standard synthesis technology using an automated DNA synthesizer.

Preferably, the nucleic acid of the present invention includes the nucleotide sequences represented by SEQ ID NOS: 15, 17, 19, and 21. The nucleic acid of the present invention not only includes the nucleotide sequences represented by SEQ ID NOS: 15, 17, 19, and 21, but also includes all the sequences which have a sequence homology of at least 70% to the above sequences, preferably at least 80%, more preferably at least 90%, even more preferably at least 95%, and most preferably at least 98%, and the peptide encoded by the above nucleic acid can bind to in vivo receptors of insulin, thereby exhibiting a biological activity substantially the same as that of insulin.

As used herein, the term "homology" refers to a degree of similarity with a given amino acid sequence of a native wild-type protein or a polynucleotide sequence encoding the same, and includes those sequences which have the identity of the above-described percentages or higher to the amino acid sequences or polynucleotide sequences of the present invention. The homology may be determined by comparing the two given sequences by the naked eye or may be determined using a bioinformatic algorithm which enables the analysis of a homology by arranging the subject sequences for comparison. The homology between the two given amino acid sequences may be indicated as a percentage. The useful automated algorithm is available for use in GAP, BESTFIT, FASTA, and TFASTA computer software modules of Wisconsin Genetics Software Package (Genetics Computer Group, Madison, Wis., USA). The arrangement algorithm automated in the above modules includes sequence arrangement algorithms by Needleman & Wunsch, Pearson & Lipman, and Smith & Waterman. Other useful algorithms on sequence arrangement and homology determination are automated in software including FASTP, BLAST, BLAST2, PSIBLAST, and CLUSTAL W.

In another aspect, the present invention provides a recombinant vector including a nucleic acid encoding the insulin analog. The recombinant vector according to the present invention may be constructed as a vector for conventional cloning or expression, and may be constructed as a vector to use a prokaryotic cell or a eukaryotic cell as a host cell.

As used herein, the term "vector" refers to a recombinant vector capable of expressing a target protein in an appropriate host cell, which is a gene construct including essential regulatory factors operably linked to enable the expression of a nucleic acid insert. The present invention can prepare a recombinant vector which includes a nucleic acid encoding an insulin analog, and the insulin analog of the present invention may be obtained via transformation or transfection of the recombinant vector into a host cell.

In the present invention, the nucleic acid encoding the insulin analog is operably linked to a promoter. As used herein, the term "operably linked" refers to a functional connection between a regulatory sequence for nucleic acid expression (e.g., a promoter, a signal sequence, a ribosome-binding site, a transcription termination sequence, etc.) and a different nucleotide sequence, and the regulatory sequence can regulate the transcription and/or translation of the different nucleotide sequence by the same.

As used herein, the term "promoter" refers to an untranslated nucleic acid sequence located upstream of a coding region, which includes a polymerase-binding site and has the activity of initiating transcription of a gene located downstream of a promoter into mRNA, i.e., a DNA domain to which polymerase binds and initiates the transcription of a gene, and it is located at the 5' domain of mRNA transcription initiation.

For example, when the vector of the present invention is a recombinant vector and uses a prokaryotic cell as a host cell, in general, a strong promoter (e.g., tac promoter, lac promoter, lacUV5 promoter, lpp promoter, pLλ promoter, pRλ promoter, racy promoter, amp promoter, recA promoter, SP6 promoter, trp promoter, T7 promoter, etc.) capable of executing transcription, a ribosome-binding site for the initiation of translation, and transcription/translation termination sequences should be included.

Additionally, the vector to be used in the present invention may be prepared by manipulating the plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4-λB, λ-Charon, λΔz1, M13, etc.), or viruses (e.g., SV40, etc.) which are commonly used in the art.

Meanwhile, when the vector of the present invention is a recombinant vector and uses a eukaryotic cell as a host cell, promoters derived from the genomes of mammalian cells (e.g., metallothionein promoter) or promoters derived from the mammalian viruses (e.g., adenovirus late promoter, 7.5K promoter of papillomavirus, SV40 promoter, cytomegalovirus promoter, and tk promoter of HSV) may be used, and in general, the vector includes a polyadenylated sequence (e.g., bovine growth hormone terminator and a polyadenylated sequence derived from SV40) as a transcription termination sequence.

Additionally, the recombinant vector of the present invention includes an antibiotic-resistance gene commonly used in the art as a selective marker, and may include, for example, genes having resistance to ampicillin, gentamycin, carbenicillin, chloramphenicol, streptomycin, kanamycin, geneticin, neomycin, and tetracycline.

The recombinant vector of the present invention may additionally include a different sequence to make it easy to purify target proteins being collected, i.e., a single-chain insulin analog, proinsulin, or an analog thereof. The sequence to be additionally included may be a tag sequence for protein purification, e.g., glutathione S-transferase (Pharmacia, USA), a maltose-binding protein (NEB, USA), FLAG (IBI, USA), 6-histidine, etc., but the kinds of the sequence necessary for the purification of target proteins are not limited thereto.

Fusion proteins expressed by the recombinant vector including the above tag sequence may be purified by affinity chromatography. For example, when glutathione 5-transferase is fused, glutathione, which is the substrate of the enzyme, may be used, and when 6-histidine tag is used, a desired target protein may be easily collected by a Ni-NTA column.

In still another aspect, the present invention provides a transformant transformed by a recombinant vector including the nucleic acid encoding the insulin analog.

As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, the Hanahan method with improved efficiency using dimethyl sulfoxide (DMSO) as a reducing agent in the $CaCl_2$ precipitation method, electroporation, a CaPO$_4$ precipitation method, a protoplast fusion method, a stirring method using silicon carbide fiber, an agrobacteria-mediated transformation, a transformation using PEG, dextran sulfate-, lipofectamine-, and dry/suppression-mediated transformations, etc.

The method for transforming the recombinant vector including a nucleic acid encoding an insulin analog according to the present invention may not be limited to these methods, but any method for transformation or transfection commonly used in the art may be used without limitation.

The transformant of the present invention may be obtained by introducing a recombinant vector including the target nucleic acid which encodes an insulin analog into a host cell.

An appropriate host to be used in the present invention may not be particularly limited as long as it can express the nucleic acid of the present invention. Examples of the appropriate host may include a bacteria belonging to the genus *Escherichia* such as *E. coli*, a bacteria belonging to the genus *Bacillus* such as *Bacillus subtilis*, a bacteria belonging to the genus *Pseudomonas* such as *Pseudomonas putida*, yeasts such as *Pichia pastoris, Saccharomyces cerevisiae*, and *Schizosaccharomyces pombe*, an insect cell such as *Spodoptera frugiperda* (SF9), and animal cells such as CHO, COS, and BSC. Preferably, *E. coli* is used as a host cell.

In an exemplary embodiment, the respective nucleotide sequence encoding the insulin analogs 1 to 3 according to the present invention was amplified via PCR, and the amplified gene fragments were cloned into pET22b vector (Novagen). For the expression of the insulin analogs in the form of an inclusion body in a cell, the pET22b vector was treated with restriction enzymes, NdeI and BamHI, to remove a signal sequence therein, the PCR-amplified products of the insulin analogs were treated with the same restriction enzymes, NdeI and BamHI, and the respective isolated DNA was inserted into the pET22b cloning vector using T4 DNA ligase. The thus-obtained expression vectors were named as pET22b-insulin analogs 1 to 4, respectively.

The expression vector pET22b-insulin analogs 1 to 4 respectively encode amino acid sequences represented by SEQ ID NOS: 16, 18, 20, and 22, under the control of T7 promoter, and each of the insulin analogs was expressed in the form of an inclusion body in a host cell, respectively.

The recombinant vector pET22b-insulin analogs 1 to 4 including nucleic acids encoding each of the insulin analogs of SEQ ID NOS: 16, 18, 20, and 22 were transformed into *E. coli*, respectively, and thereby transformants expressing them in the form of an inclusion body were obtained.

In still another aspect, the present invention provides a method for preparing an insulin analog using the transformants.

Preferably, the present invention provides a method for preparing an insulin analog, including:

a) preparing a recombinant expression vector including a nucleic acid encoding the insulin analog;

b) transforming the recombinant expression vector into a host cell and obtaining a transformant therefrom;

c) culturing the transformant and expressing the insulin analog; and d) isolating and purifying the expressed insulin analog peptide.

The medium used in culturing the transformants in the present invention should meet the requirements for host cell cultivation in an appropriate manner. The carbon sources to be contained in the medium for the growth of a host cell may be appropriately selected by the decision of a skilled person in the art according to the transformants prepared thereof, and appropriate cultivation conditions may be selected to control the period and amount of cultivation.

Examples of the sugar source to be used may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These materials may be used alone or in combination.

Examples of the nitrogen source to be used may include peptone, yeast extract, meat gravy, malt extract, corn steep liquor, soybean flour, and urea, or inorganic compounds such as ammonium sulfate, ammonium chloride, ammonium phosphate, ammonium carbonate, and ammonium nitrate. The nitrogen source may also be used alone or in combination.

Examples of the phosphorous source to be used may include potassium dihydrogen phosphate or dipotassium hydrogen phosphate or a corresponding sodium-containing salt. Additionally, the culture media may contain a metal salt such as magnesium sulfate or iron sulfate necessary for the growth of the transformant. Furthermore, essential growth materials such as amino acids and vitamins may be used. Furthermore, appropriate precursors for culture media may also be used. The above sources may be appropriately added to a culture during cultivation by a batch culture or continuous culture. The pH of the culture may be appropriately adjusted using a basic compound such as sodium hydroxide, potassium hydroxide, and ammonia, or an acid compound such as phosphoric acid or sulfuric acid. Additionally, an antifoaming agent such as fatty acid polyglycol ester may be added to prevent foam generation. Additionally, in order to maintain the aerobic state of the culture, oxygen or an oxygen-containing gas (e.g., air) may be injected into the culture. The transformant of the present invention may be cultured at 20° C. to 45° C., and preferably, 25° C. to 40° C. Additionally, the cultivation is continued until the maximum amount of production of the desired insulin analogs is obtained, and in this regard, the cultivation may normally be continued for 10 hours to 160 hours.

As described above, the transformant of the present invention can produce insulin analogs when appropriate culture conditions are provided according to host cells, and the peptide-N-glycosidase produced thereof according to the vector constitution and characteristics of a host cell may be secreted within the cytoplasm or into the periplasmic space of the host cell or extracellularly.

The proteins expressed within or outside of the host cell may be purified by a conventional method.

Examples of the purification method may include salting-out (e.g., ammonium sulfate precipitation, ammonium phosphate precipitation, etc.), solvent precipitation (e.g., protein fraction precipitation using acetone or ethanol, etc.), dialysis, gel filtration, ion exchange, or chromatography such as reversed column chromatography, ultrafiltration, etc., and these methods may be used alone or in combination.

The transformant of the present invention is characterized in that the insulin analogs 1 to 3 are expressed from the recombinant vector pET22b-insulin analogs 1 to 3 in the form of an inclusion body under the control of T7 promoter. Accordingly, it is preferable that the insulin analogs 1 to 3, which were expressed in the form of an inclusion body, are converted into a soluble form and then isolated and purified.

In an exemplary embodiment, the present invention may further include the following steps for isolating and purifying the insulin analogs expressed in the form of an inclusion body from the transformant:

d-1) obtaining the transformant cells from the culture and pulverizing the same;

d-2) recovering the expressed insulin analog peptide from the pulverized cell lysate followed by refolding the same;

d-3) purifying the refolded insulin analog peptide by cation exchange chromatography;

d-4) treating the purified insulin analog peptide with trypsin and carboxypeptidase B; and d-5) sequentially purifying the treated insulin analog peptide by cation exchange chromatography and anion exchange chromatography.

In still another aspect, the present invention provides a pharmaceutical composition for treating diabetes containing the above-mentioned insulin analogs.

The pharmaceutical composition containing the insulin analogs according to the present invention may contain a pharmaceutically acceptable carrier. Examples of the pharmaceutically acceptable carrier for oral administration may include a binder, a glidant, a disintegrating agent, an excipient, a solubilizing agent, a dispersing agent, a stabilizing agent, a suspending agent, a coloring agent, a flavoring agent, etc.; for injection formulations, a buffering agent, a preserving agent, an analgesic, an isotonic agent, a stabilizing agent, etc. may be mixed for use; and for topical formulations, a base, an excipient, a lubricant, a preserving agent, etc. may be used. The formulation type of the pharmaceutical composition according to the present invention may be prepared variously by combination with the pharmaceutically acceptable carriers described above. For example, for oral administration, the pharmaceutical composition may be formulated into tablets, troches, capsules, elixirs, suspensions, syrups, wafers, etc. For injections, the pharmaceutical composition may be formulated into single-dose ampoules or multidose containers. Additionally, the pharmaceutical composition may also be formulated into solutions, suspensions, tablets, pills, capsules, and sustained-release formulations.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the pharmaceutical composition of the present invention may further contain a filler, an anti-coagulant, a lubricant, a humectant, a flavoring agent, an emulsifier, a preservative, etc.

In still another aspect, the present invention provides a method for treating diabetes including administering a pharmaceutical composition containing the insulin analogs of the present invention to a subject in need thereof.

The insulin analogs according to the present invention exhibit a significantly improved in vitro effect compared with that of native insulin, and thus it is expected that the administration of a pharmaceutical composition containing the above insulin analogs can be effective for treating diabetes.

As used herein, the term "administration" refers to introduction of a particular material to a patient by an appropriate manner, and the conjugate of the present invention may be administered via any of the common routes as long as the drug can arrive at a target tissue. For example, intraperitoneal, intravenous, intramuscular, subcutaneous, intradermal, oral, topical, intranasal, intrapulmonary, and intrarectal administration may be performed, but the administration route is not limited thereto. However, since peptides are digested upon oral administration, active ingredients of a composition for oral administration should be coated or formulated for protection against degradation in the stomach. Preferably, the present composition may be administered in an injectable form. In addition, the pharmaceutical composition may be administered using a certain apparatus capable of transporting the active ingredients into a target cell.

Additionally, the pharmaceutical composition of the present invention may be determined by the types of the drug as an active component as well as by several related factors including the types of diseases to be treated, administration routes, age, sex, and weight of a patient, and severity of the illness. Since the pharmaceutical composition of the present invention has excellent in vivo duration and titer, it can considerably reduce the administration frequency and dose of pharmaceutical drugs of the present invention.

Advantageous Effects of the Invention

The insulin analogs according to the present invention exhibit a significantly improved in vitro effect compared with that of native insulin, and thus the administration of the insulin analogs is expected to provide sufficient treatment even in a small amount, and can thus be effectively used for treating diabetes.

BRIEF DESCRIPTION OF THE DRAWINGS

FIG. 1 shows a result of the purity of insulin analogs according to the present invention analyzed by protein electrophoresis, and representatively, a result of the insulin analog 1 (Lane 1: size marker, and Lane 2: insulin analog 1).

FIG. 2 shows a result of the purity of insulin analogs according to the present invention analyzed by reversed phase chromatography and size exclusion chromatography, and representatively, a result of the insulin analog 1.

FIG. 3 shows a result of peptide mapping of the analogs according to the present invention, and representatively, a result of the insulin analog 1, wherein USP-insulin indicates native insulin used as control. Top: A chain (SEQ ID NO: 3), B chain (SEQ ID NO: 2). Bottom: A chain (SEQ ID NO: 1), B chain (SEQ ID NO: 2).

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Construction of an Expression Vector for Insulin Analogs

In order to construct insulin analogs in which amino acid(s) of the A-chain and/or the B-chain of native insulin were modified, primer pairs consisting of a forward primer and a reverse primer for amplifying the insulin analogs introduced with the corresponding modification were synthesized, and PCR was then performed using proinsulin cDNA as a template. In particular, the template used was that in which proinsulin cDNA (SC128255, OriGene) (see sequences: BC005255.1 and AAH05255) was cloned into pET22b vector (Novagen), and for smooth recombinant expression of insulin, the nucleotide sequence of SEQ ID NO: 23 (ATG GCA ACA ACA TCA ACA GCA ACT ACG CGT), which encodes the amino acid sequence of Met Ala Thr Thr Ser Thr Ala Thr Thr Arg (SEQ ID NO: 24), was inserted into the cloned proinsulin cDNA as a N-terminal fusion partner.

Specifically, in the present invention, the following insulin analogs including the amino acid modifications shown in Table 1 were synthesized.

TABLE 1

| | Amino Acid Modification |
|---|---|
| Insulin Analog 1 | $A^{14}$ Tyr → Glu |
| Insulin Analog 2 | $A^{14}$ Tyr → Asn |
| Insulin Analog 3 | $A^{14}$ Tyr → Glu + $B^{25}$ deletion |
| Insulin Analog 4 | $A^{14}$ Tyr → Ala + $B^{16}$ Tyr → Glu, $B^{25}$ deletion |

In Table 1 above, the insulin analog 1 is an analog which includes a substitution of the $14^{th}$ amino acid in the amino acid sequence of the A-chain of native insulin represented by SEQ ID NO: 1, i.e., tyrosine, with glutamic acid;

the insulin analog 2 is an analog which includes a substitution of the $14^{th}$ amino acid in the amino acid sequence of the A-chain of native insulin represented by SEQ ID NO: 1, i.e., tyrosine, with asparagine;

the insulin analog 3 is an analog which includes a substitution of the $14^{th}$ amino acid in the amino acid sequence of the A-chain of native insulin represented by SEQ ID NO: 1, i.e., tyrosine, with glutamic acid, and a deletion of the $25^{th}$ amino acid in the amino acid sequence of the B-chain of native insulin represented by SEQ ID NO: 2, i.e., phenylalanine, and the insulin analog 4 is an analog which includes a substitution of the $14^{th}$ amino acid in the amino acid sequence of the A-chain of native insulin represented by SEQ ID NO: 1, i.e., tyrosine, with alanine, and a substitution of the $16^{th}$ amino acid in the amino acid sequence of the B-chain of native insulin represented by SEQ ID NO: 2, i.e., tyrosine, with glutamic acid and a deletion of the $25^{th}$ amino acid in the amino acid sequence of the B-chain of native insulin represented by SEQ ID NO: 2, i.e., phenylalanine.

The respective primer pairs of forward primers and reverse primers designed for the amplification of the insulin analogs 1 to 3 are shown in Table 2 below.

TABLE 2

| | Sequence | SEQ ID NO |
|---|---|---|
| Insulin Analog 1 | 5'-ccagcatctgctccctcgaacagctggagaactactg-3' | 5 |
| | 5'-cagtagttctccagctgttcgagggagcagatgctgg-3' | 6 |
| Insulin Analog 2 | 5'-cagcatctgctccctcaaccagctggagaactac-3' | 7 |
| | 5'-gtagttctccagctggttgagggagcagatgctgg-3' | 8 |
| Insulin Analog 3 | 5'-ccagcatctgctccctcgaacagctggagaactactg-3' | 5 |

TABLE 2-continued

| | Sequence | SEQ ID NO |
|---|---|---|
| | 5'-cagtagttctccagctgttcgagggagcagatgctgg-3' | 6 |
| | 5'-gcggggaacgaggcttctacacacccaagacccg-3' | 9 |
| | 5'-cgggtcttgggtgtgtagaagcctcgttccccgc-3' | 10 |
| Insulin Analog 4 | 5'-cagcatctgctccctcgcccagctggagaactac-3' | 11 |
| | 5'-gtagttctccagctgggcgagggagcagatgctg-3' | 12 |
| | 5'-ctggtggaagctctcgagctagtgtgcggggaac-3' | 13 |
| | 5'-gttccccgcacactagctcgagagcttccaccag-3' | 14 |
| | 5'-gcggggaacgaggcttctacacacccaagacccg-3' | 9 |
| | 5'-cgggtcttgggtgtgtagaagcctcgttccccgc-3' | 10 |

In Table 2 above, the primer pair consisting of SEQ ID NOS: 5 and 6 was designed for the substitution of the $14^{th}$ amino acid in the amino acid sequence of the A-chain of native insulin, i.e., tyrosine, with glutamic acid; the primer pair consisting of SEQ ID NOS: 7 and 8 was designed for the substitution of the $14^{th}$ amino acid in the amino acid sequence of the A-chain of native insulin, i.e., tyrosine, with asparagine; the primer pair consisting of SEQ ID NOS: 9 and 10 was designed for the deletion of the $25^{th}$ amino acid in the amino acid sequence of the B-chain of native insulin, i.e., phenylalanine; the primer pair consisting of SEQ ID NOS: 11 and 12 was designed for the substitution of the $14^{th}$ amino acid in the amino acid sequence of the A-chain of native insulin i.e., tyrosine, with alanine; and the primer pair consisting of SEQ ID NOS: 13 and 14 was designed for the substitution of the $16^{th}$ amino acid in the amino acid sequence of the B-chain of native insulin, i.e., tyrosine, with glutamic acid In order to perform PCR for the amplification of insulin analogs which include the corresponding modifications, a reaction solution was prepared by mixing 150 ng of template DNA, 1 mL each of 100 pM primers, 5 mL of 2.5 mM dNTP, 10 units of pfx polymerase (Invitrogen, USA), and a 10× buffer solution. The reaction solution was subjected to initial denaturation at 95° C. for 30 seconds, followed by 18 repeated cycles of annealing at 95° C. for 30 seconds, 55° C. for 30 seconds, and 68° C. for 6 minutes, and it was finally left at 68° C. for 5 minutes. The thus-obtained PCR-amplified products were extracted using a gel extraction kit (Qiagen, Germany) and treated with restriction enzymes, NdeI and BamHI, to prepare insertion fragments. The pET22b vector (Novagen, USA) was then cleaved with the same restriction enzymes and fragments were extracted using the same gel extraction kit. The above insertion fragments were ligated into the thus-prepared vector using T4 ligase to prepare expression vector pET22b-insulin analogs 1 to 4. The expression vectors include nucleic acids encoding the amino acid sequences of the insulin analogs 1 to 4 under the control of T7 promoter, and the vectors can express the insulin analog proteins in the form of an inclusion body in a host cell.

The thus-obtained expression vector pET22b-insulin analog 1 according to the present invention includes nucleic acid having a nucleotide sequence represented by SEQ ID NO: 15, which encodes the insulin analog having an amino acid sequence represented by SEQ ID NO: 16; the thus-obtained expression vector pET22b-insulin analog 2 according to the present invention includes a nucleic acid having a nucleotide sequence represented by SEQ ID NO: 17 which encodes the insulin analog having an amino acid sequence represented by SEQ ID NO: 18; the thus-obtained expression vector pET22b-insulin analog 3 according to the present invention includes a nucleic acid having a nucleotide sequence represented by SEQ ID NO: 19, which encodes the insulin analog having an amino acid sequence represented by SEQ ID NO: 20; and the thus-obtained expression vector pET22b-insulin analog 4 according to the present invention includes a nucleic acid having a nucleotide sequence represented by SEQ ID NO: 21, which encodes the insulin analog having an amino acid sequence represented by SEQ ID NO: 22

The DNA sequences and protein sequences of each of the insulin analogs 1 to 3 are shown in Table 3 below.

TABLE 3

| | | Sequence | | | | | | | | SEQ ID NO |
|---|---|---|---|---|---|---|---|---|---|---|
| Insulin Analog 1 | DNA | TTC GTT AAC CAA CAC TTG TGT GGC TCA CAC CTG GTG GAA GCT CTC TAC CTA GTG TGC GGG GAA CGA GGC TTC TTC TAC CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC GAA CAG CTG GAG AAC TAC TGC AAC TGA | | | | | | | | | 15 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Glu Gln Leu Glu Asn Tyr Cys Asn | | | | | | | | | 16 |
| Insulin Analog 2 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC AAC CAG CTG GAG AAC TAC TGC AAC TGA | | | | | | | | | 17 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Asn Gln Leu Glu Asn Tyr Cys Asn | | | | | | | | | 18 |
| Insulin Analog 3 | DNA | TTC GTT AAC CAA CAC TTG TGT GGC TCA CAC CTG GTG GAA GCT CTC TAC CTA GTG TGC GGG GAA CGA GGC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC GAA CAG CTG GAG AAC TAC TGC AAC TGA | | | | | | | | | 19 |
| | Protein | Phe Val Asn Gln His Leu Cys Gly Ser His Leu Val Glu Ala Leu Tyr Leu Val Cys Gly Glu Arg Gly Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Glu Gln Leu Glu Asn Tyr Cys Asn | | | | | | | | | 20 |
| Insulin Analog 4 | DNA | TTC GTT AAC CAA CAC TTG TGT GGC TCA CAC CTG GTG GAA GCT CTC GAG CTA GTG TGC GGG GAA CGA GGC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC GCC CAG CTG GAG AAC TAC TGC AAC TGA | | | | | | | | | 21 |
| | Protein | Phe Val Asn Gln His Leu Cys Gly Ser His Leu Val Glu Ala Leu Glu Leu Val Cys Gly Glu Arg Gly Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Ala Gln Leu Glu Asn Tyr Cys Asn | | | | | | | | | 22 |

Example 2: Expression of Recombinant Insulin Analogs

The recombinant expression of insulin analogs according to the present invention under the control of T7 promoter was performed as follows. E. coli BL21-DE3 (E. coli B F-dcm ompT hsdS(rB⁻mB⁻) gal λDE3) (Novagen, USA) was transformed with each of the insulin analog expression vectors prepared in Example 1. Transformation was performed using a method recommended by Novagen, the manufacturer of E. coli BL21-DE3. Each single colony transformed with the insulin analog expression vectors was collected, inoculated into a 2× Luria Broth (LB) medium containing 50 μg/mL ampicillin, and cultured at 37° C. for 15 hours. The recombinant E. coli culture and the 2× LB medium containing 30% glycerol were mixed in a 1:1 (v/v) ratio, aliquoted 1 mL of the mixture into each cryo-tube, respectively, and stored at −140° C. The resultant was used as a cell stock for producing recombinant insulin analogs.

For the expression of recombinant insulin analogs, one vial of each cell stock was dissolved in 500 mL of 2× LB and incubated in a shaking water bath maintained at 37° C. for 14 hours to 16 hours. The incubation was stopped when the OD value reached 5.0 or higher, and the culture was used as a seed culture. The seed culture was inoculated into 17 L of a fermentation medium using a 50 L fermenter (MSJ-U2, B.E. MARUBISHI, Japan) and the initial batch fermentation was started. The cultivation was performed at 37° C. at a stirring rate of 500 rpm with 20 L/min (1 vvm) of air supply while maintaining the pH at 6.70 with 30% ammonia water. Regarding the progress of the fermentation, when the nutrients in the culture medium were limited, the fermentation was carried out in a fed-batch culture by adding a feeding solution. The growth of bacteria was monitored based on OD values, and when the OD value reached 100 or higher, IPTG at a final concentration of 500 μM was introduced therein. The cultivation was continued further for about 23 hours to 25 hours after the introduction. Upon termination of the cultivation, the recombinant bacteria was recovered by centrifugation and stored at −80° C. until use.

Example 3: Isolation and Purification of Recombinant Insulin Analogs

For the isolation and purification of the recombinant insulin analogs expressed in Example 2 from the transformants, cells were disrupted as shown below followed by refolding in order to change the insulin analogs expressed in the form of a water-insoluble inclusion body to a water-soluble form.

<3-1> Recovery and Refolding of Recombinant Insulin Analogs

Specifically, each cell pellet was resuspended in a 1 L solubilizing buffer solution (50 mM Tris-HCl (pH 9.0), 1 mM EDTA (pH 8.0), 0.2 M NaCl, and 0.5% Triton X-100), and the cells were disrupted using a microfluidizer M-110EH (AC Technology Corp. Model M1475C) at a pressure of 15,000 psi. The disrupted cell lysates were centrifuged at 7,000 rpm and 4° C. for 20 minutes and the supernatant was discarded. The resultant was resuspended in 3 L of a washing buffer (0.5% Triton X-100, 50 mM Tris (pH 8.0), 0.2 M NaCl, and 1 mM EDTA). Centrifugation was performed at 7,000 rpm and 4° C. for 20 minutes, and the resulting pellet was resuspended in distilled water, followed by centrifugation in the same manner. Each of the resulting pellets was resuspended in 400 mL of a buffer solution (1 M glycine, 3.78 g cysteine-HCl, pH 10.6) and stirred at room temperature for 1 hour. In order to recover the resuspended recombinant insulin analogs, 400 mL of 8 M urea was added thereto and stirred at 40° C. for 1 hour. For the refolding of the solubilized recombinant insulin analogs, the resultant was centrifuged at 7,000 rpm and 4° C. for 20 minutes, and the supernatant was recovered. The supernatant was stirred at 4° C. for 16 hours while 7.2 L of distilled water was added using a peristaltic pump at a flow rate of 1000 mL/hour.

<3-2> Purification of Cation Exchange Chromatography

The samples in which the refolding was completed in Example <3-1> were respectively loaded into a cation exchange column (Source S, GE Healthcare), which was equilibrated with a 20 mM sodium citrate buffer solution (pH 2.0) containing 45% ethanol to be conjugated thereto. Insulin analog proteins were then eluted from the column with a linear concentration gradient from 0% to 100% in 10 column volumes using a 20 mM sodium citrate buffer solution (pH 2.0) which contained 0.5 M potassium chloride and 45% ethanol.

<3-3> Treatment with Trypsin and Carboxypeptidase B

Salts were removed from the samples eluted in Example <3-2> using a desalting column, followed by replacement of a buffer solution (10 mM Tris-HCl, pH 8.0). The samples were treated with trypsin, which corresponds to a molar ratio of 1000 relative to the protein amount of the sample, and carboxypeptidase B, which corresponds to a molar ratio of 2000 relative to the protein amount of the sample, and stirred at 16° C. for 16 hours. The reaction was stopped by lowering the pH to 3.5 using 1 M sodium citrate (pH 2.0).

<3-4> Purification of Cation Exchange Chromatography

The samples in which the reaction was completed in Example <3-3> were respectively reloaded into a cation exchange column (Source S, GE Healthcare) which was equilibrated with a 20 mM sodium citrate buffer solution (pH 2.0) containing 45% ethanol to be conjugated thereto. Insulin analog proteins were then eluted from the column with a linear concentration gradient from 0% to 100% in 10 column volumes using a 20 mM sodium citrate buffer solution (pH 2.0) which contained 0.5 M potassium chloride and 45% ethanol.

<3-5> Purification of Anion Exchange Chromatography

Salts were removed from the samples eluted in Example <3-4> using a desalting column, followed by replacement of a buffer solution (10 mM Tris-HCl, pH 7.5). For the isolation of pure insulin analogs from the thus-obtained samples, the resultants were respectively loaded into an anion exchange column (Source Q, GE Healthcare) equilibrated with a 10 mM Tris buffer solution (pH 7.5) to be conjugated. Insulin analog proteins were then eluted from the column with a linear concentration gradient from 0% to 100% in 10 column volumes using a 10 mM Tris buffer solution (pH 7.5) which contained 0.5 M sodium chloride.

The purity of the purified insulin analogs was analyzed via protein electrophoresis (SDS-PAGE) and reversed phase and size exclusion chromatography, and the results are shown in FIG. 1 and FIG. 2, respectively. Additionally, the modifications in amino acids were confirmed by peptide mapping and the analysis of molecular weight of each peak, and the results are shown in FIG. 3.

As a result, it was confirmed that there was a modification in an amino acid sequence for each of the insulin analogs according to their desired purposes.

Example 4: Comparison of In Vitro Effect Between Native Insulin and Insulin Analogs In order to measure the in vitro effect of the insulin analogs isolated and purified in Example 3, an experiment on glucose absorption capability (glucose uptake or lipid synthesis capability) was performed using a mouse-derived 3T3-L1 cell line, which was differentiated into adipocytes. The 3T3-L1 cell line (ATCC, CL-173) was subcultured using Dulbecco's Modified Eagle's Medium (DMEM, Gibco, Cat. No. 12430) containing 10% bovine newborn calf serum (NBCS) two to three times per week. The 3T3-L1 cell line was suspended in a differentiation medium (DMEM containing 10% FBS), inoculated into a 48-well plate at a concentration of $5 \times 10^4$ cells/well, and cultured at 37° C. for 48 hours. For the differentiation of the 3T3-L1 cell line into adipocytes, the differentiation medium was treated with 1 μg/mL of human insulin (Sigma, Cat. No. 19278), 0.5 mM IBMX (3-isobutyl-1-methylxanthine, Sigma, Cat. No. 15879), and 1 μM dexamethasone (Sigma, Cat. No. D4902), and the existing medium was removed and the mixture was aliquoted into each well in the amount of 250 μL/well. Forty-eight hours thereafter, the medium was replaced with a differentiation medium to which only 1 μg/mL of human insulin was added. The induction of differentiation of the 3T3-L1 cell line into adipocytes was then confirmed for a period of 7 to 9 days while replacing the medium with the differentiation medium containing 1 μg/mL of human insulin at 48 hour intervals.

For the experiment on glucose absorption capability, the cells which completed their differentiation into adipocytes were washed once with a serum-free DMEM medium, and then treated with 250 μL of the serum-free DMEM medium for 4 hours to induce serum depletion therein.

Human insulin and insulin analogs were respectively subjected to a 10-fold serial dilution from 5 μM to 0.005 nM using serum-free DMEM medium to be used as samples. The thus-prepared insulin samples were respectively added into cells in an amount of 250 μL, and cultured at 37° C. for 24 hours in a 5% $CO_2$ incubator. In order to measure the remaining glucose amount in the medium for which cultivation was completed, each culture sample was collected in an amount of 200 μL, diluted 5-fold using D-PBS, and subjected to the GOPOD analysis (GOPOD Assay Kit, Megazyme, Cat. No. K-GLUC). The concentration of the remaining glucose was calculated based on the absorbance of a glucose standard solution, the $EC_{50}$ values on glucose uptake capability of the insulin analogs were respectively calculated, and the results are shown in Table 4 below.

TABLE 4

|  | Glucose Uptake Capability (relative to native insulin) (%) |
| --- | --- |
| Native Human Insulin | 100 |
| Insulin Analog 1 | 238.4 |
| Insulin Analog 2 | 241.7 |
| Insulin Analog 3 | 705 |

As shown in Table 4, the insulin analog 1 showed a 238.4% increase of glucose uptake capability, the insulin analog 2 showed a 241.7% increase, and the insulin analog 3 showed a 705% increase, compared with that of native insulin, respectively, From the above results, it was confirmed that the insulin analogs according to the present invention exhibit a remarkable in vitro effect of a 2- to 7-fold increase compared with that of native insulin, and these results indicate that the insulin analogs can significantly increase their in vivo serum half-life and can thus be provided as stable insulin formulations, thus being effectively used as a therapeutic agent for treating diabetes.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. An insulin analog peptide comprising an A-chain of SEQ ID NO: 3 indicated in the following General Formula 1 and a B-chain of SEQ ID NO: 4 indicated in the following General Formula 2:

(General Formula 1)

Xaa1-Ile-Val-Glu-Xaa2-Cys-Cys-Thr-Ser-Ile-Cys-Xaa3-Leu-Xaa4-Gln-Xaa5-Glu-Asn-Xaa6-Cys-Xaa7    (SEQ ID NO: 3)

wherein
Xaa1 is alanine, glycine, glutamine, histidine, glutamic acid, or asparagine;
Xaa2 is alanine, glutamic acid, glutamine, histidine, or asparagine;
Xaa3 is alanine, serine, glutamine, histidine, or asparagine;
Xaa4 is aspartic acid;
Xaa5 is alanine, leucine, tyrosine, histidine, or asparagine;
Xaa6 is alanine, tyrosine, serine, glutamic acid, histidine, or asparagine; and
Xaa7 is asparagine, glycine, histidine, or alanine; and (General Formula 2)

Phe-Val-Asn-Gln-His-Leu-Cys-Gly-Ser-His-Leu-Val-Glu-Ala-Leu-Xaa8-Leu-Val-Cys-Gly-Glu-Arg-Gly-Phe-Xaa9-Tyr-Xaa10-Xaa11-Lys-Thr    (SEQ ID NO: 4)

wherein
Xaa8 is tyrosine or is absent;
Xaa9 is phenylalanine or is absent;
Xaa10 is threonine; and
Xaa11 is proline or glutamic acid.

2. The insulin analog peptide of claim 1, wherein, in the B-chain of SEQ ID NO: 4, Xaa8 is tyrosine, Xaa9 is absent, and Xaa10 is threonine.

3. A pharmaceutical composition comprising the insulin analog peptide according to claim 1 and a pharmaceutically acceptable carrier.

4. A method of preparing the insulin analog peptide according to claim 1, comprising:
   a) preparing a recombinant expression vector comprising a nucleic acid encoding the insulin analog peptide according to claim 1;
   b) transforming the recombinant expression vector into a host cell and obtaining a transformant therefrom;
   c) culturing the transformant and expressing the insulin analog peptide; and
   d) isolating and purifying the expressed insulin analog peptide.

5. The method of claim 4, wherein the transformant is *E. coli*.

6. The method of claim 4, wherein the isolating and purifying comprise:
   d-1) obtaining the transformant cells from the culture and pulverizing the same;
   d-2) recovering the expressed insulin analog peptide from the pulverized cell lysate followed by refolding the same;
   d-3) purifying the refolded insulin analog peptide by cation exchange chromatography;
   d-4) treating the purified insulin analog peptide with trypsin and carboxypeptidase B; and
   d-5) sequentially purifying the treated insulin analog peptide by cation exchange chromatography and anion exchange chromatography.

* * * * *